(12) United States Patent
Southern

(10) Patent No.: US 7,888,494 B2
(45) Date of Patent: Feb. 15, 2011

(54) ANALYSING POLYNUCLEOTIDE SEQUENCES

(75) Inventor: Edwin Southern, Oxford (GB)

(73) Assignee: Oxford Gene Therapy Limited, Oxford (GB)

( * ) Notice: Subject to any disclaimer, the term of this patent is extended or adjusted under 35 U.S.C. 154(b) by 1928 days.

(21) Appl. No.: 10/772,467

(22) Filed: Feb. 6, 2004

(65) Prior Publication Data

US 2004/0259119 A1 Dec. 23, 2004
US 2009/0142751 A2 Jun. 4, 2009

Related U.S. Application Data

(60) Division of application No. 09/422,803, filed on Oct. 22, 1999, now abandoned, which is a division of application No. 08/925,676, filed on Sep. 9, 1997, now Pat. No. 6,054,270, which is a division of application No. 08/230,012, filed on Apr. 19, 1994, now Pat. No. 5,700,637, which is a continuation of application No. 08/695,682, filed on May 3, 1991, now abandoned, which is a continuation-in-part of application No. 07/573,317, filed as application No. PCT/GB89/00460 on May 2, 1989, now abandoned.

(30) Foreign Application Priority Data

May 3, 1988 (GB) ................................. 8810400.5

(51) Int. Cl.
*C07H 21/02* (2006.01)
*C07H 21/04* (2006.01)
*C12M 1/18* (2006.01)
*C12Q 1/68* (2006.01)

(52) U.S. Cl. ................. 536/24.3; 435/287.2; 435/288.4; 435/6

(58) Field of Classification Search ........................ None
See application file for complete search history.

(56) References Cited

U.S. PATENT DOCUMENTS

| | | | |
|---|---|---|---|
| 4,000,252 A | 12/1976 | Kosak | |
| 4,145,406 A | 3/1979 | Schick et al. | |
| 4,205,952 A | 6/1980 | Cais | |
| 4,216,245 A | 8/1980 | Johnson | |
| 4,254,082 A | 3/1981 | Schick et al. | |
| 4,299,916 A | 11/1981 | Litman et al. | |
| 4,323,647 A | 4/1982 | Monji et al. | |
| 4,327,073 A | 4/1982 | Huang | |
| 4,395,486 A | 7/1983 | Wilson et al. | |
| 4,442,204 A | 4/1984 | Greenquist et al. | |
| 4,451,433 A | 5/1984 | Yamashita et al. | ............ 422/63 |
| 4,458,066 A | 7/1984 | Caruthers | |
| 4,483,964 A | 11/1984 | Urdea et al. | |
| 4,563,419 A | 1/1986 | Ranki et al. | |
| 4,591,550 A | 5/1986 | Hafeman et al. | |
| 4,591,570 A | 5/1986 | Chang | ........................ 436/518 |
| 4,656,127 A | 4/1987 | Mundy | |
| 4,689,405 A | 8/1987 | Frank et al. | |
| 4,703,008 A | 10/1987 | Lin | |
| 4,704,353 A | 11/1987 | Humphries et al. | |
| 4,719,176 A | 1/1988 | Klotz | |
| 4,728,502 A | 3/1988 | Hamill | |
| 4,731,325 A | 3/1988 | Palva et al. | |
| 4,737,464 A | 4/1988 | McConnell et al. | |
| 4,789,630 A | 12/1988 | Bloch et al. | |
| 4,828,386 A * | 5/1989 | Matkovich et al. | .......... 356/246 |
| 4,849,330 A | 7/1989 | Humphries et al. | ............ 435/4 |
| 4,877,745 A | 10/1989 | Hayes et al. | |
| 4,883,579 A | 11/1989 | Humphries et al. | |
| 4,888,278 A | 12/1989 | Singer et al. | |
| 4,961,915 A | 10/1990 | Martin | ....................... 422/116 |
| 4,963,815 A | 10/1990 | Hafeman | |
| 4,968,602 A | 11/1990 | Dattagupta | ..................... 435/6 |
| 4,981,783 A | 1/1991 | Augenlicht | |
| 4,994,373 A | 2/1991 | Stavrianopoulos et al. | ..... 435/6 |
| 5,002,867 A | 3/1991 | Macevicz | |
| 5,126,276 A | 6/1992 | Fish et al. | |
| 5,164,319 A | 11/1992 | Hafeman et al. | |
| 5,202,231 A | 4/1993 | Drmanac et al. | |

(Continued)

FOREIGN PATENT DOCUMENTS

CA 1284931 1/1991

(Continued)

OTHER PUBLICATIONS

U.B. Voss et al., Biochemical Society Transactions, 624th Meeting, Dublin, pp. 216-217, 1987.

(Continued)

*Primary Examiner*—Marjorie Moran
*Assistant Examiner*—Anna Skibinsky
(74) *Attorney, Agent, or Firm*—Wenderoth, Lind & Ponack, L.L.P.

(57) ABSTRACT

An apparatus is provided for analysing a polynucleotide. The apparatus includes: a support having an impermeable surface; porous material attached to the impermeable surface; and an array of oligonucleotides with predetermined sequences attached to the porous material. The array includes at least two defined cells, the sequence of the oligonucleotides of a first cell being different from the sequence of the oligonucleotides of a second cell, and the oligonucleotides being shorter than the polynucleotide.

22 Claims, No Drawings

U.S. PATENT DOCUMENTS

| | | | |
|---|---|---|---|
| 5,348,855 | A | 9/1994 | Dattagupta et al. |
| 5,429,807 | A | 7/1995 | Matson et al. ............. 422/131 |
| 5,474,796 | A | 12/1995 | Brennan .................... 427/2.13 |
| 5,486,452 | A | 1/1996 | Gordon et al. ................. 435/5 |
| 5,700,637 | A | 12/1997 | Southern |
| 6,054,270 | A | 4/2000 | Southern |

FOREIGN PATENT DOCUMENTS

| | | | |
|---|---|---|---|
| CA | 1284931 | | 6/1991 |
| EP | 0 063 810 | | 11/1982 |
| EP | 0063810 | | 11/1982 |
| EP | 0063810 | A1 | 11/1982 |
| EP | 0 130 523 | | 1/1985 |
| EP | 0 130 739 | | 1/1985 |
| EP | 0130523 | A3 | 1/1985 |
| EP | 0130739 | A2 | 1/1985 |
| EP | 0 142 299 | | 5/1985 |
| EP | 0142299 | A2 | 5/1985 |
| EP | 0 171 150 | | 2/1986 |
| EP | 0171150 | | 2/1986 |
| EP | 0171150 | B1 | 2/1986 |
| EP | 0 194 132 | | 9/1986 |
| EP | 0194132 | A2 | 9/1986 |
| EP | 0 197 266 | | 10/1986 |
| EP | 0 228 075 | | 7/1987 |
| EP | 0228075 | A2 | 7/1987 |
| EP | 0 235 726 | | 9/1987 |
| EP | 0 237 362 | | 9/1987 |
| EP | 0 238 332 | | 9/1987 |
| EP | 0 235726 | A3 | 9/1987 |
| EP | 0235726 | | 9/1987 |
| EP | 237362 | | 9/1987 |
| EP | 0238332 | A2 | 9/1987 |
| EP | 0 268 237 | | 5/1988 |
| EP | 0268237 | A2 | 5/1988 |
| EP | 0 281 927 | | 9/1988 |
| EP | 0281927 | A2 | 9/1988 |
| EP | 0 304 202 | | 2/1989 |
| EP | 0 305 929 | | 3/1989 |
| EP | 0 386 229 | | 9/1990 |
| EP | 0 392 546 | | 10/1990 |
| EP | 0 373 203 | | 8/1994 |
| EP | 0 119 573 | A1 | 9/1994 |
| GB | 1 526 708 | | 9/1978 |
| GB | 2 156 074 | | 10/1985 |
| GB | 2 197 720 | | 5/1988 |
| WO | 83/01459 | | 4/1983 |
| WO | 84/01031 | | 3/1984 |
| WO | 84/03151 | | 8/1984 |
| WO | 84/03564 | | 9/1984 |
| WO | 85/01051 | | 3/1985 |
| WO | 86/00991 | | 2/1986 |
| WO | 86/03782 | | 7/1986 |
| WO | 86/06487 | | 11/1986 |
| WO | 88/01302 | | 2/1988 |
| WO | 89/11548 | | 11/1989 |
| WO | 90/15070 | | 12/1990 |
| WO | 92/10092 | | 6/1992 |
| WO | 93/22480 | | 11/1993 |
| YU | 570/87 | | 8/1990 |

OTHER PUBLICATIONS

Roche Award Molecular Bioanalytics, 2004 to Professor Edwin Southern et al., pp. 1-4, 2004.

Wodicka et al., "Genome-wide expression monitoring in *Saccharomyces cerevisiaer*", Nature Biotechnology, vol. 15, pp. 1359-1367, 1997.

David Kitchin QC and Richard Meade, Affymetrix' Opening Submissions, in the United Kingdom litigation between *Oxford Gene Technology (OGT)* v. *Affymetrix*, case Nos. HC 1999 02517, HC 1999 04645, pp. 1-81, Mar. 22, 2001, London, United Kingdom.

Bird & Bird, Notice to Admit Facts, in the United Kingdom litigation between *Oxford Gene Technology (OGT)* v. *Affymetrix*, case No. HC 1999 04645, pp. 1-5, Jan. 28, 2000, London, United Kingdom.

Richard Meade, Bristows, Second Defendant's Response to the Claimant's Notice to Admit Facts, in the United Kingdom litigation between *Oxford Gene Technology (OGT)* v. *Affymetrix*, case No. HC 1999 04645, pp. 1-3, Jun. 22, 2000, London, United Kingdom.

Bristows, Particulars of Independently Valid Claims, in the United Kingdom litigation between *Oxford Gene Technology (OGT)* v. *Affymetrix*, case No. HC 1999 04645, pp. 1-2, Jun. 22, 2000, London, United Kingdom.

Richard Meade, Bristows, Statement of Reasons, in the United Kingdom litigation between *Oxford Gene Technology (OGT)* v. *Affymetrix*, case No. HC 1999 04645, pp. 1-4, Jun. 30, 2000, London, United Kingdom.

Bird & Bird, Statement of Opposition, in the United Kingdom litigation between *Oxford Gene Technology (OGT)* v. *Affymetrix*, case No. HC 1999 04645, pp. 1-5, Jun. 30, 2000, London, United Kingdom.

Bird & Bird, Re-Re-Re-Amended Particulars of Objections, in the United Kingdom litigation between *Oxford Gene Technology (OGT)* v. *Affymetrix*, case No. HC 1999 04645, pp. 1-5, Mar. 13, 2001, London, United Kingdom.

Alastair Wilson QC, Amended Particulars of Claim, in the United Kingdom litigation between *Oxford Gene Technology (OGT)* v. *Affymetrix*, case No. HC 1999 02517, pp. 1-11, Nov. 26, 1999, Oxford, United Kingdom.

Bird & Bird, Amended Particulars of Infringement, in the United Kingdom litigation between *Oxford Gene Technology (OGT)* v. *Affymetrix*, case No. HC 1999 02517, pp. 12-14, Sep. 1, 2000, London, United Kingdom.

Richard Meade, Defence and Counterclaim of the First and Second Defendants, in the United Kingdom litigation between *Oxford Gene Technology (OGT)* v. *Affymetrix*, case No. HC 1999 02517, pp. 1-6, Aug. 6, 1999, London, United Kingdom.

Richard Meade, Amended Particulars of Objections of the First and Second Defendants, in the United Kingdom litigation between *Oxford Gene Technology (OGT)* v. *Affymetrix*, case No. HC 1999 02517, pp. 21-37, Jan. 15, 2001, London, United Kingdom.

Manches, Re-Re-Re-Amended Reply and Defence of Counterclaim, in the United Kingdom litigation between *Oxford Gene Technology (OGT)* v. *Affymetrix*, case No. HC 1999 02517, pp. 38-46, Mar. 2000, Oxford, United Kingdom.

Dr. David R. Bentley, Summary of Expert Report, in the United Kingdom litigation between *Oxford Gene Technology (OGT)* v. *Affymetrix*, case Nos. HC 1999 04645 and HC 1999 02517, pp. 1-38, Jan. 30, 2001, London, United Kingdom.

Dr. David R. Bentley, Expert Report of Dr. David Bentley, in the United Kingdom litigation between *Oxford Gene Technology (OGT)* v. *Affymetrix*, case Nos. HC 1999 04645 and HC 1999 02517, pp. 1A-1F, pp. 1-124, Jan. 30, 2001, London, United Kingdom.

Dr. David R. Bentley, Annex 1 to Expert Report of Dr. David Bentley, in the United Kingdom litigation between *Oxford Gene Technology (OGT)* v. *Affymetrix*, case Nos. HC 1999 04645 and HC 1999 02517, pp. 1-17, Jan. 30, 2001, London, United Kingdom.

Dr. David R. Bentley, Annex 2 to Expert Report of Dr. David Bentley, in the United Kingdom litigation between *Oxford Gene Technology (OGT)* v. *Affymetrix*, case Nos. HC 1999 04645 and HC 1999 02517, pp. 1-2, Jan. 30, 2001, London, United Kingdom.

Dr. David R. Bentley, Annex 3 to Expert Report of Dr. David Bentley, in the United Kingdom litigation between *Oxford Gene Technology (OGT)* v. *Affymetrix*, case Nos. HC 1999 04645 and HC 1999 02517, pp. 1-2, Jan. 30, 2001, London, United Kingdom.

Dr. David R. Bentley, Annex 4 to Expert Report of Dr. David Bentley, in the United Kingdom litigation between *Oxford Gene Technology (OGT)* v. *Affymetrix*, case Nos. HC 1999 04645 and HC 1999 02517, pp. 1-4, Jan. 30, 2001, London, United Kingdom.

Dr. David R. Bentley, Annex 5 to Expert Report of Dr. David Bentley, in the United Kingdom litigation between *Oxford Gene Technology (OGT)* v. *Affymetrix*, case Nos. HC 1999 04645 and HC 1999 02517, pp. 1-12, Jan. 30, 2001, London, United Kingdom.

Dr. David R. Bentley, Annex 6 to Expert Report of Dr. David Bentley, in the United Kingdom litigation between *Oxford Gene Technology (OGT)* v. *Affymetrix*, case Nos. HC 1999 04645 and HC 1999 02517, pp. 1-8, Jan. 30, 2001, London, United Kingdom.

Dr. David R. Bentley, Annex 7 to Expert Report of Dr. David Bentley, in the United Kingdom litigation between *Oxford Gene Technology (OGT)* v. *Affymetrix*, case Nos. HC 1999 04645 and HC 1999 02517, pp. 1-2, Jan. 30, 2001, London, United Kingdom.

Dr. David R. Bentley, Annex 8 to Expert Report of Dr. David Bentley, in the United Kingdom litigation between *Oxford Gene Technology (OGT)* v. *Affymetrix*, case Nos. HC 1999 04645 and HC 1999 02517, pp. 1-6, Jan. 30, 2001, London, United Kingdom.

Dr. David R. Bentley, Annex 9 to Expert Report of Dr. David Bentley, in the United Kingdom litigation between *Oxford Gene Technology (OGT)* v. *Affymetrix*, case Nos. HC 1999 04645 and HC 1999 02517, pp. 1-12, Jan. 30, 2001, London, United Kingdom.

Dr. David R. Bentley, Annex 10 to Expert Report of Dr. David Bentley, in the United Kingdom litigation between *Oxford Gene Technology (OGT)* v. *Affymetrix*, case Nos. HC 1999 04645 and HC 1999 02517, pp. 1-14, Jan. 30, 2001, London, United Kingdom.

Dr. David R. Bentley, Annex 11 to Expert Report of Dr. David Bentley, in the United Kingdom litigation between *Oxford Gene Technology (OGT)* v. *Affymetrix*, case Nos. HC 1999 04645 and HC 1999 02517, pp. 1-5, Jan. 30, 2001, London, United Kingdom.

Dr. David R. Bentley, Annex 12 to Expert Report of Dr. David Bentley, in the United Kingdom litigation between *Oxford Gene Technology (OGT)* v. *Affymetrix*, case Nos. HC 1999 04645 and HC 1999 02517, pp. 1-6, Jan. 30, 2001, London, United Kingdom.

Dr. David R. Bentley, Annex 13 to Expert Report of Dr. David Bentley, in the United Kingdom litigation between *Oxford Gene Technology (OGT)* v. *Affymetrix*, case Nos. HC 1999 04645 and HC 1999 02517, pp. 1-8, Jan. 30, 2001, London, United Kingdom.

Dr. David R. Bentley, Annex 14 to Expert Report of Dr. David Bentley, in the United Kingdom litigation between *Oxford Gene Technology (OGT)* v. *Affymetrix*, case Nos. HC 1999 04645 and HC 1999 02517, pp. 1-8, Jan. 30, 2001, London, United Kingdom.

Dr. David R. Bentley, Annex 15 to Expert Report of Dr. David Bentley, in the United Kingdom litigation between *Oxford Gene Technology (OGT)* v. *Affymetrix*, case Nos. HC 1999 04645 and HC 1999 02517, pp. 1-4, Jan. 30, 2001, London, United Kingdom.

Dr. David R. Bentley, Annex 16 to Expert Report of Dr. David Bentley, in the United Kingdom litigation between *Oxford Gene Technology (OGT)* v. *Affymetrix*, case Nos. HC 1999 04645 and HC 1999 02517, pp. 1-38, Jan. 30, 2001, London, United Kingdom.

Dr. David R. Bentley, Annex 17 to Expert Report of Dr. David Bentley, in the United Kingdom litigation between *Oxford Gene Technology (OGT)* v. *Affymetrix*, case Nos. HC 1999 04645 and HC 1999 02517, pp. 1-4, Jan. 30, 2001, London, United Kingdom.

Dr. David R. Bentley, Annex 18 to Expert Report of Dr. David Bentley, in the United Kingdom litigation between *Oxford Gene Technology (OGT)* v. *Affymetrix*, case Nos. HC 1999 04645 and HC 1999 02517, pp. 1-2, Jan. 30, 2001, London, United Kingdom.

Dr. David R. Bentley, Annex 19 to Expert Report of Dr. David Bentley, in the United Kingdom litigation between *Oxford Gene Technology (OGT)* v. *Affymetrix*, case Nos. HC 1999 04645 and HC 1999 02517, pp. 1-4, Jan. 30, 2001, London, United Kingdom.

Prof. Wolfgang Pfleiderer, Expert Report and Annex 1, in the United Kingdom litigation between *Oxford Gene Technology (OGT)* v. *Affymetrix*, case Nos. HC 1999 04645 and HC 1999 02517, pp. 1-40 and 1-2, Jan. 19, 2001, Konstanz, Germany.

Dr. David B. Wallace, Expert Report of David Bowen Wallace, P.E., PH.D., in the United Kingdom litigation between *Oxford Gene Technology (OGT)* v. *Affymetrix*, case Nos. HC 1999 04645 and HC 1999 02517, pp. 1-55, Jan. 18, 2001, London, United Kingdom.

Dr. David B. Wallace, Annex 1 to Expert Report of David Bowen Wallace, P.E., PH.D., in the United Kingdom litigation between *Oxford Gene Technology (OGT)* v. *Affymetrix*, case Nos. HC 1999 04645 and HC 1999 02517, pp. 1-25, Jan. 18, 2001, London, United Kingdom.

Dr. David B. Wallace, Annex 2 to Expert Report of David Bowen Wallace, P.E., PH.D., in the United Kingdom litigation between *Oxford Gene Technology (OGT)* v. *Affymetrix*, case Nos. HC 1999 04645 and HC 1999 02517, pp. 1-24, Jan. 18, 2001, London, United Kingdom.

Dr. Paul H. Silverman, Statement of Dr. Paul Hyman Silverman and Exhibit PS-1, in the United Kingdom litigation between *Oxford Gene Technology (OGT)* v. *Affymetrix*, case Nos. HC 1999 04645 and HC 1999 02517, pp. 1-2 and 1-8, Nov. 22, 2000, Irvine, California.

Prof. Edwin M. Southern, First Witness Statement of Edwin Mellor Southern, in the United Kingdom litigation between *Oxford Gene Technology (OGT)* v. *Affymetrix*, case Nos. HC 1999 04645, pp. 1-10, May 1, 2000, Oxford, United Kingdom.

Prof. Edwin M. Southern, Exhibit EMS-1 to First Witness Statement of Edwin Mellor Southern, in the United Kingdom litigation between *Oxford Gene Technology (OGT)* v. *Affymetrix*, case Nos. HC 1999 04645, pp. 1-14, May 1, 2000, Oxford, United Kingdom.

Prof. Edwin M. Southern, Exhibit EMS-2 to First Witness Statement of Edwin Mellor Southern, in the United Kingdom litigation between *Oxford Gene Technology (OGT)* v. *Affymetrix*, case Nos. HC 1999 04645, pp. 1-41, May 1, 2000, Oxford, United Kingdom.

Prof. Edwin M. Southern, Exhibit EMS-3 to First Witness Statement of Edwin Mellor Southern, in the United Kingdom litigation between *Oxford Gene Technology (OGT)* v. *Affymetrix*, case Nos. HC 1999 04645, pp. 1-58, May 1, 2000, Oxford, United Kingdom.

Prof. Edwin M. Southern, Fifth Witness Statement of Edwin Mellor Southern, in the United Kingdom litigation between *Oxford Gene Technology (OGT)* v. *Affymetrix*, case Nos. HC 1999 04645, pp. 1-13, Jan. 22, 2001, Oxford, United Kingdom.

Prof. Edwin M. Southern, Annex 4 to Fifth Witness Statement of Edwin Mellor Southern, in the United Kingdom litigation between *Oxford Gene Technology (OGT)* v. *Affymetrix*, case Nos. HC 1999 04645, pp. 1-7, Jan. 22, 2001, Oxford, United Kingdom.

Peter Jay Coassin, Witness Statement of Peter Jay Coassin, in the United Kingdom litigation between *Oxford Gene Technology (OGT)* v. *Affymetrix*, case Nos. HC 1999 02517, pp. 1-4, Jan. 22, 2001, Fullerton, California.

Dr. Timothy S. Fell, Witness Statement of Timothy Stephen Fell, in the United Kingdom litigation between *Oxford Gene Technology (OGT)* v. *Affymetrix*, case Nos. HC 1999 02517, pp. 1-11, Jan. 18, 2001, Oxford, United Kingdom.

Dr. Timothy S. Fell, Annex 1 to Witness Statement of Timothy Stephen Fell, in the United Kingdom litigation between *Oxford Gene Technology (OGT)* v. *Affymetrix*, case Nos. HC 1999 02517, pp. 1-5, Jan. 18, 2001, Oxford, United Kingdom.

Dr. Timothy S. Fell, Annex 2 to Witness Statement of Timothy Stephen Fell, in the United Kingdom litigation between *Oxford Gene Technology (OGT)* v. *Affymetrix*, case Nos. HC 1999 02517, pp. 1-6, Jan. 18, 2001, Oxford, United Kingdom.

Dr. Timothy S. Fell, Annex 3 to Witness Statement of Timothy Stephen Fell, in the United Kingdom litigation between *Oxford Gene Technology (OGT)* v. *Affymetrix*, case Nos. HC 1999 02517, pp. 1-8, Jan. 18, 2001, Oxford, United Kingdom.

Dr. Timothy S. Fell, Annex 4 to Witness Statement of Timothy Stephen Fell, in the United Kingdom litigation between *Oxford Gene Technology (OGT)* v. *Affymetrix*, case Nos. HC 1999 02517, pp. 1-11, Jan. 18, 2001, Oxford, United Kingdom.

Dr. Timothy S. Fell, Annex 5 to Witness Statement of Timothy Stephen Fell, in the United Kingdom litigation between *Oxford Gene Technology (OGT)* v. *Affymetrix*, case Nos. HC 1999 02517, pp. 1-2, Jan. 18, 2001, Oxford, United Kingdom.

Dr. Timothy S. Fell, Annex 6 to Witness Statement of Timothy Stephen Fell, in the United Kingdom litigation between *Oxford Gene Technology (OGT)* v. *Affymetrix*, case Nos. HC 1999 02517, pp. 1-11, Jan. 18, 2001, Oxford, United Kingdom.

Stewart L. Huxley, Witness Statement of Stewart Leonard Huxley, in the United Kingdom litigation between *Oxford Gene Technology (OGT)* v. *Affymetrix*, case Nos. HC 1999 02517, pp. 1-2, Jan. 8, 2001, Oxford, United Kingdom.

Martin G. Johnson, Witness Statement of Martin George Johnson, in the United Kingdom litigation between *Oxford Gene Technology (OGT)* v. *Affymetrix*, case Nos. HC 1999 02517, pp. 1-7, Jan. 19, 2001, Oxford, United Kingdom.

Ekins R., "Multi-analyte immunoassay", Journal of Pharmaceutical & Biomedical Analysis, Vo. 7, No. 2, pp. 155-168, 1989.

Kimura et al., "An Immobilized Enzyme Membrane Fabrication Method using an Ink Jet Nozzle", Biosensors; vol. 4, pp. 41-52, 1988.

Geysen et al., "Strategies for epitope analysis using peptide synthesis", Journal of Immunological Methods, vol. 102, pp. 259-274, 1987.

Monaco et al., "Human Genome Linking With Cosmids and Yeast Artificial Chromosomes", abstract from CSHS, p. 90, 1989.

Dr. Edwin Southern, Statutory Declaration of Dr. Edwin Southern, in the Opposition Proceedings against EP No. 0 619 321, pp. 1-17, Oct. 1999, Kidlington, United Kingdom.

Ekins R., "Why we should move towards non-isotopic immunoassay?", Presentation at International Symposium on Molecular Probes: Technology and Medical Applications, pp. 1-22, Apr. 11-13, 1988, Florence, Italy.

Lysov et al., "A New Method for Determining the DNA Nucleotide Sequence by Hybridization with Oligonucleotides", Doklady Biochemistry, vol. 303, pp. 436-438, Nov.-Dec. 1988.

Professor Edwin Southern, Witness Statement of Professor Edwin Mellor Southern, in the United Kingdom litigation between *Oxford Gene Technology (OGT)* v. *Affymetrix*, case No. HC 1999 02517, pp. 1-40, Jan. 2000, Kidlington, United Kingdom.

Bird and Bird, Notice of Opposition, in the Opposition Proceedings against EP No. 0 619 321 filed by Oxford Gene Technology, pp. 1-15, Oct. 1999, London, United Kingdom.

Dr. Edwin Southern, Statutory Declaration of Dr. Edwin Southern, in the Opposition Proceedings against EP No. 0 619 321, pp. 1-17, Oct. 1999, Oxford, United Kingdom.

Morris, Nichols, Arsht & Tunnell, Defendant's Motion for Leave to File a Second Amended Answer, in the United States litigation between *Oxford Gene Technology (OGT)* v. *Affymetrix*, U.S. District Court for the District of Delaware, CA No. 99-348, pp. 1-16, Apr. 2000, Wilmington, Delaware.

Dale Davis, Expert Report of Dale Davis, in the United States litigation between *Oxford Gene Technology (OGT)* v. *Affymetrix*, U.S. District Court for the District of Delaware, CA No. 99-348, pp. 1-37, Aug. 2000, Wilmington, Delaware.

Grant Morgan, Expert Report of Grant Morgan, in the United States litigation between *Oxford Gene Technology (OGT)* v. *Affymetrix*, U.S. District Court for the District of Delaware, CA No. 99-348, pp. 1-15, Aug. 2000, Atascadero, California.

Dr. Elias Corey, Expert Report of Dr. Elias James Corey, in the United States litigation between *Oxford Gene Technology (OGT)* v. *Affymetrix*, U.S. District Court for the District of Delaware, CA No. 99-348, pp. 1-10, Aug. 2000, Wilmington, Delaware.

Dr. James Wetmur, Expert Report of Dr. James G. Wetmur, in the United States litigation between *Oxford Gene Technology (OGT)* v. *Affymetrix*, U.S. District Court for the District of Delaware, CA No. 99-348, pp. 1-29, Aug. 2000, Wilmington, Delaware.

Morris, Nichols, Arsht & Tunnell, Memorandum of Points and Authorities in Support of Affymetrix's Opposition to OGT's Motion for Summary Judgment of Validity, in the United States litigation between *Oxford Gene Technology (OGT)* v. *Affymetrix*, U.S. District Court for the District of Delaware, CA No. 99-348, pp. 1-13, Sep. 2000, Wilmington, Delaware.

Dr. James Wetmur, Declaration of James G. Wetmur in Support of Affymetrix's Opposition to OGT's Motion for Summary Judgment of Validity, in the United States litigation between *Oxford Gene Technology (OGT)* v. *Affymetrix*, U.S. District Court for the District of Delaware, CA No. 99-348, p. 1, Sep. 2000, Palo Alto, California.

Dr. James Wetmur, Expert Rebuttal Report of Dr. James G. Wetmur, in the United States litigation between *Oxford Gene Technology (OGT)* v. *Affymetrix*, U.S. District Court for the District of Delaware, CA No. 99-348, pp. 1-45, Sep. 2000, Palo Alto, California.

Dr. Martin Adelman, Expert Report—Martin J. Adelman, in the United States litigation between *Oxford Gene Technology (OGT)* v. *Affymetrix*, U.S. District Court for the District of Delaware, CA No. 99-348, pp. 1-16, Aug. 2000, Washington, D.C.

Dr. Elias Corey, Declaration of Dr. Elias James Corey in Support of Affymetrix' Opposition to OGT's Motion for Summary Judgment of Validity, in the United States litigation between *Oxford Gene Technology (OGT)* v. *Affymetrix*, U.S. District Court of Delaware, CA No. 99-348, p. 1, Sep. 2000, Cambridge, Massachusetts.

Pretrial Order Exhibits 1-5 and 12-13, in the United States litigation between *Oxford Gene Technology (OGT)* v. *Affymetrix*, U.S. District Court for the District of Delaware, CA No. 99-348, pp. 1-110, Oct. 2000, Wilmington, Delaware.

Transcript of Markman Hearing, in the United States litigation between *Oxford Gene Technology (OGT)* v. *Affymetrix*, U.S. District Court for the District of Delaware, CA No. 99-348, pp. 1-149, Oct. 2000, Wilmington, Delaware.

Wada A., Abstracts of Presentations at International Workshop on Automatic and High Speed DNA Base Sequencing, pp. 2-11, Jul. 7-9, 1987, Okayama, Japan.

Wallace et al., "Hybridization of synthetic oligodeoxyribonucleotides to phi and 174 DNA: the effect of single base pair mismatch", Nucleic Acids Research, vol. 6, No. 11, pp. 3543-3557, 1979.

Uwe Maskos, "A novel method of nucleic acid sequence analysis", Maskos Thesis submitted to University of Oxford, pp. 2-161, New College, Oxford, 1991.

Bannworth, W. et al., "A System for the Simultaneous Chemical Synthesis of Different DNA Fragments on Solid Support", DNA, vol. 5, No. 5, pp. 413-419, 1986.

Lohrmann, R. et al., "New Solid Supports for DNA Synthesis", Fourth Annual Congress for Recombinant DNA Research, p. 122, 1984.

Goldkorn, T. et al., "A simple and efficient enzymatic method for covalent attachment of DNA to cellulose; Application for hybridization-restriction analysis and for in vitro synthesis of DNA probes", Nucleic Acids Research, Vo. 14, No. 22, pp. 9171-9191, 1986.

Duncan, C. et al., "Affinity Chromatography of a Sequence-specific DNA Binding Protein Using Teflon-linked Oligonucleotides", Analytical Biochemistry, Vo. 169, pp. 104-108, 1988.

Voss et al., "A simple and efficient method for covalently attaching oligonucleotides to a cellulose support matrix", Biochemical Society Transactions, 165th meeting, London, pp. 367-368, 1987.

Nicholls, P. et al., "Nucleic Acid Analysis by Sandwich Hybridization", Journal of Clinical Laboratory Analysis, vol. 3, pp. 122-135, 1989.

Wallace, R. et al., "The use of synthetic oligonucleotides as hybridization probes. II. Hybridization of oligonucleotides of mixed sequence to rabbit beta-globin DNA", Nucleic Acids Research, vol. 9, No. 4, pp. 879-894, 1981.

File wrapper of U.S. Appl. No. 07/593,589 now abandoned.

File wrapper of U.S. Appl. No. 07/772,625 maturing into US 5,348,855 on Sep. 1994 to Dattagupta et al.

Sproat, B. et al., "A new linkage for solid phase synthesis of oligonucleotides", Nucleic Acids Research, vol. 13, No. 8, pp. 2979-2987, 1985.

Kremsky, J. et al., "Immobilization of DNA via oligonucleotides containing an aldehyde or carboxylic acid group at the 5' terminus", Nucleic Acids Research, vol. 15, No. 7, pp. 2891-2909, 1987.

Wolf, S. et al., "Rapid hybridization kinetics of DNA attached to submicron latex particles", Nucleic Acids Research, vol. 15; No. 7, pp. 2911-2926, 1987.

Atkinson, T., "A convenient procedure for the synthesis of oligodeoxyribonucleotide affinity columns for isolation of mRNA", Nucleic Acids Research, vol. 16, No. 13, p. 6232, 1988.

Court Transcript of Technology Tutorial, in the United States litigation between *Oxford Gene Technology (OGT)* v. *Mergen Ltd* et al., U.S. District Court for the District of Delaware, CA No. 02-1695, pp. 1-72, Dec. 2003, Wilmington, Delaware.

Blank Rome LLP, OGT's Technology Tutorial, in the United States litigation between *Oxford Gene Technology (OGT)* v. *Mergen Ltd* et al., U.S. District Court for the District of Delaware, CA No. 02-1695, pp. 1-28, Dec. 2003, Wilmington, Delaware.

Ashby & Geddes, Defendant Mergen, Ltd.'s Slide Presentation for the Dec. 18, 2003 Tutorial, in the United States litigation between *Oxford Gene Technology (OGT)* v. *Mergen Ltd* et al., U.S. District Court of Delaware, CA No. 02-1695, pp. 1-11, Dec. 2003, Wilmington, Delaware.

Patton Boggs LLP, Defendant Clontech Laboratories Slide Presentation for the Dec. 18, 2003 Tutorial, in the United States litigation between *Oxford Gene Technology (OGT)* v. *Mergen Ltd* et al., U.S.

District Court for the District of Delaware, CA No. 02-1695, pp. 1-33, Dec. 2003, Wilmington, Delaware.

Kirkland & Ellis LLP, Letter to Perkins Coie LLP enclosing OGT's Claim Terms, in the United States litigation between *Oxford Gene Technology (OGT)* v. *Mergen Ltd* et al., U.S. District Court for the District of Delaware, CA No. 02-1695, pp. 1-6, Apr. 2004, Chicago, Illinois.

Perkins Coie LLP, Mergen Ltd.'s Claim Terms and Proposed Construction, in the United States litigation between *Oxford Gene Technology (OGT)* v. *Mergen Ltd* et al., U.S. District Court for the District of Delaware, CA No. 01-1695, pp. 1-7, Apr. 2004, Menlo Park, California.

Dr. Paul Purdue, Expert Report of Paul Edward Purdue Ph.D., in the United States litigation between *Oxford Gene Technology (OGT)* v. *Mergen Ltd* et al., U.S. District Court for the District of Delaware, CA No. 02-1695, pp. 1-10, May 2004, New York, NY.

Dr. Paul Purdue, Expert Report of Paul Edward Purdue Ph.D., in the United States litigation between *Oxford Gene Technology (OGT)* v. *Mergen Ltd* et al., U.S. District Court for the District of Delaware, CA No. 02-1695, pp. 1-13, Jun. 2004, New York, NY.

Potter Anderson & Corroon LLP, Defendant Mergen Ltd.'s Third Set of Supplemental Responses to Oxford Gene Technology Ltd's First and Second Set of Interrogatories, in the United States litigation between *Oxford Gene Technology (OGT)* v. *Mergen Ltd* et al., U.S. District Court for the District of Delaware, CA No. 02-1695, pp. 1-45, Jun. 2004, Wilmington, Delaware.

Blank Rome LLP, Oxford Gene Technology Ltd.'s Claim Construction Brief, in the United States litigation between *Oxford Gene Technology (OGT)* v. *Mergen Ltd* et al., U.S. District Court for the District of Delaware, CA No. 02-1695, pp. 1-186, Jul. 2004, Wilmington, Delaware.

Potter Anderson & Corroon LLP, Mergen Limited's Opening Claim Construction Brief, in the United States litigation between *Oxford Gene Technology (OGT)* v. *Mergen Ltd* et al., U.S. District Court for the District of Delaware, CA No. 02-1695, pp. 1-37, Jul. 2004, Wilmington, Delaware.

Potter Anderson & Corroon LLP, Mergen Limited's Reply in Support of its Motion for Summary Judgment of invalidity of Claim 1 of United States Patent No. 6,054,270 Pursuant to 35 U.S.C. 112, in the United States litigation between *Oxford Gene Technology (OGT)* v. *Mergen Ltd* et al., U.S. District Court for the District of Delaware, CA No. 02-1695, pp. 1-9, Aug. 2004, Wilmington, Delaware.

Potter Anderson & Corroon LLP, Declaration of Norbert Stahl in Support of Mergen Limited's Reply Brief in Support of its Motion for Summary Judgment of Invalidity of Claim 1 of United States Patent No. 6,054,270 Pursuant to 35 U.S.C. 112, in the United States litigation between *Oxford Gene Technology (OGT)* v. *Mergen Ltd* et al., U.S. District Court for the District of Delaware, CA No. 02-1695, pp. 1-58, Aug. 2004, Wilmington, Delaware.

Blank Rome LLP, Oxford Gene Technology's Claim Construction Brief In Response to Mergen's Claim Construction Briefing, in the United States litigation between *Oxford Gene Technology (OGT)* v. *Mergen Ltd* et al., U.S. District Court for the District of Delaware, CA No. 02-1695, pp. 1-118, Aug. 2004, Wilmington, Delaware.

Order and Memorandum Opinion of the U.S. District Court on Claim Construction, in the United States litigation between *Oxford Gene Technology (OGT)* v. *Mergen Ltd* et al., U.S. District Court for the District of Delaware, CA No. 02-1695, pp. 1-20, Sep. 2004, Wilmington, Delaware.

Order and Memorandum Opinion of the U.S. District Court on Expert Reports, in the United States litigation between *Oxford Gene Technology (OGT)* v. *Mergen Ltd* et al., U.S. District Court for the District of Delaware, CA No. 02-1695, pp. 1-23, Nov. 2004, Wilmington, Delaware.

Order and Memorandum Opinion of the U.S. District Court on Summary Judgment, in the United States litigation between *Oxford Gene Technology (OGT)* v. *Mergen Ltd* et al., U.S. District Court for the District of Delaware, CA No. 02-1695, pp. 1-39, Nov. 2004, Wilmington, Delaware.

Potter Anderson & Corroon LLP, Mergen Limited's Motion for Reconsideration of the Court's Order Granting in Part Oxford Gene Technology Limited's Motion for Partial Summary Judgment of Infringement, in the United States litigation between *Oxford Gene Technology (OGT)* v. *Mergen Ltd* et al., U.S. District Court for the District of Delaware, CA No. 02-1695, pp. 1-16, Dec. 2004, Wilmington, Delaware.

Blank Rome LLP, Oxford Gene Technology Limited's Opposition to Mergen Limited's Motion for Reconsideration, in the United States litigation between *Oxford Gene Technology (OGT)* v. *Mergen Ltd* et al., U.S. District Court for the District of Delaware, CA No. 02-1695, pp. 1-28, Dec. 2004, Wilmington, Delaware.

Potter Anderson & Corroon LLP, Mergen Limited's Reply in Support of its Motion for Reconsideration of the Court's Order, in the United States litigation between *Oxford Gene Technology (OGT)* v. *Mergen Ltd* et al., U.S. District Court for the District of Delaware, CA No. 02-1695, pp. 1-8, Dec. 2004, Wilmington, Delaware.

Blank Rome LLP, Letter to Judge Jordan re claim terms, in the United States litigation between *Oxford Gene Technology (OGT)* v. *Mergen Ltd* et al., U.S. District Court for the District of Delaware, CA No. 02-1695, pp. 1-2, Jan. 2005, Wilmington, Delaware.

Order of the U.S. District Court on Mergen's Motion for Reconsideration, in the United States litigation between *Oxford Gene Technology (OGT)* v. *Mergen Ltd* et al., U.S. District Court for the District of Delaware, CA No. 02-1695, pp. 1-5, Jan. 2005, Wilmington, Delaware.

Khrapko, K. et al., "An oligonucleotide hybridization approach to DNA sequencing", FEBS, vol. 256, Nos. 1-2, pp. 118-122, Oct. 1989.

Potter Anderson & Corroon LLP, Telechem International, Inc.'s Responses to Oxford Gene Technology Ltd's First Set of Interrogatories, in the United States litigation between *Oxford Gene Technology (OGT)* v. *Telechem International* et al., U.S. District Court for the District of Delaware, CA No. 04-013, pp. 1-22, Oct. 2004, Wilmington, Delaware.

Polsky-Cynkin, R. et al., "Use of DNA Immobilized on Plastic and Agarose Supports to Detect DNA by Sandwich Hybridization", Clinical Chemistry, vol. 31, No. 9, pp. 1438-1443, 1985.

Michael Best & Friedrich LLP, Oxford Gene Technology Limited's Opening Markman Brief, in the United States litigation between *Oxford Gene Technology (OGT)* v. *Motorola, Inc.*, U.S. District Court for the Northeastern District of Illinois, CA No. 02-9344, pp. 1-81, Dec. 2003, Chicago, Illinois.

Brinks Hofer Gilson & Lione, Motorola's Response Markman Brief, in the United States litigation between *Oxford Gene Technology (OGT)* v. *Motorola, Inc.*, U.S. District Court for the Northeastern District of Illinois, CA No. 02-9344, pp. 1-39, Jan. 2004, Chicago, Illinois.

Brinks Hofer Gilson & Lione, Motorola's Response Markman Brief, Exhibits A-Z, the United States litigation between *Oxford Gene Technology (OGT)* v. *Motorola, Inc.*, U.S. District Court for the Northeastern District of Illinois, CA No. 02-9344, pp. 1-195, Jan. 2004, Chicago, Illinois.

Brinks Hofer Gilson & Lione, Motorola's Response Markman Brief, Exhibits A(1)-G(1), the United States litigation between *Oxford Gene Technology (OGT)* v. *Motorola, Inc.*, U.S. District Court for the Northeastern District of Illinois, CA No. 02-9344, pp. 1-51, Jan. 2004, Chicago, Illinois.

Brinks Hofer Gilson & Lione, Motorola's Response Markman Brief, Exhibits 1-3, the United States litigation between *Oxford Gene Technology (OGT)* v. *Motorola, Inc.*, U.S. District Court for the Northeastern District of Illinois, CA No. 02-9344, pp. 1-23, Jan. 2004, Chicago, Illinois.

Michael Best & Friedrich LLP, OGT's Reply to Markman Brief, in the United States litigation between *Oxford Gene Technology (OGT)* v. *Motorola, Inc.*, U.S. District Court for the Northeastern District of Illinois, CA No. 02-9344, pp. 1-21, Mar. 2004, Chicago, Illinois.

Michael Best & Friedrich LLP, OGT's Exhibit A Claim Chart, in the United States litigation between *Oxford Gene Technology (OGT)* v. *Motorola, Inc.*, U.S. District Court for the Northeastern District of Illinois, CA No. 02-9344, pp. 1-10, Mar. 2004, Chicago, Illinois.

Michael Best & Friedrich LLP, OGT's Exhibit 1-9, in the United States litigation between *Oxford Gene Technology (OGT)* v. *Motorola, Inc.*, U.S. District Court for the Northeastern District of Illinois, CA No. 02-9344, pp. 1-139, Mar. 2004, Chicago, Illinois.

Michael Best & Friedrich LLP, OGT's Exhibit H-R, in the United States litigation between *Oxford Gene Technology (OGT)* v.

*Motorola, Inc.*, U.S. District Court for the Northeastern District of Illinois, CA No. 02-9344, pp. 1-222, Mar. 2004, Chicago, Illinois.
Civil Docket for CA No. 99-0348, *Oxford Gene Technology (OGT)* v. *Affymetrix, Inc.*, U.S. District Court for Delaware, pp. 1-36, Apr. 2005, Wilmington, Delaware.
Civil Docket for CA No. 02-1695, *Oxford Gene Technology (OGT)* v. *Mergen, Ltd.*, U.S. District Court for Delaware, pp. 1-31, Apr. 2005, Wilmington, Delaware.
Civil Docket for CA No. 04-0013, *Oxford Gene Technology (OGT)* v. *Telechem International, Inc.*, U.S. District Court for Delaware, pp. 1-7, Apr. 2005, Wilmington, Delaware.
Civil Docket for CA No. 02-1687, *Oxford Gene Technology (OGT)* v. *Nanogen, Inc.*, U.S. District Court for Delaware, pp. 1-5, Apr. 2005, Wilmington, Delaware.
Civil Docket for CA No. 02-9344, *Oxford Gene Technology (OGT)* v. *Motorola, Inc.*, U.S. District Court for the Northeastern District of Illinois, pp. 1-4, Apr. 2005, Chicago, Illinois.
Declaration from Radomir Crkvenjakov (with four exhibits), Sep. 1996.
Declaration from Ivan Labat, Sep. 1996.
Statement from the Institute of Molecular Genetics and Genetic Engineering (IMGGE) in Belgrade, Sep. 1996.
Statement by Professor Roger Ekins (with an abstract of a lecture given by him on Apr. 11, 1988 at a symposium, and a post-published paper corresponding to said lecture), Dec. 1996.
Statutory Declaration of Dr. Nichlolas Vaughan Ashely (with Exhibit NVA1), May 1995.
Statutory Declaration of Dr. William Bains (with Exhibits WB1, WB2 and WB3), May 1995.
Declaration of Professor Lubert Stryer, Jan. 1997.
Statutory Declaration of Dr. William Bains, Jan. 1997.
Statutory Declaration of Dr. Nicholas Vaughan Ashley, Jan. 1997.
Declaration of Edwin Mellor Southern (with Exhibits EMS1 and EMS2), Jan. 1998.
Declaration of Dr. Thomas Gingeras, Jan. 1999.
Declaration of Professor Calvin Quate, Jan. 1999.
Declaration of Dr. Glenn Mc Gall, Jan. 1999.
Declaration of Edwin Mellor Southern, Jul. 2001.
Bird & Bird, "Claimant's Notice of Experiments", in the United Kingdom Litigation between *Oxford Gene Technology (OGT)* v. *Affymetrix*, case No. HC 1999 02517, pp. 1-12, Jul. 31, 2000, London, United Kingdom.
Declaration of Marvin Stodolsky, Oct. 1996.
M. S. Urdea et al., "A novel method for the rapid detection of specific nucleotide sequences in crude biological samples without blotting or radioactivity; application to the analysis of hepatitis B virus in human serum", Gene, vol. 61, 1987, pp. 253-264.
C. G. Miyada et al., "Oligonucleotide Hybridization Techniques", Methods in Enzymology, vol. 154, No. 6, 1987, pp. 94-107.
E. Calva et al., "Analysis of the in vitro Synthesis of 5'-γ-$^{32}$ P-labeled Transcripts from Coliphage λ by Gel Electrophoresis, RNA-DNA Hybridization, and RNase T1 Digestion", The Journal of Biological Chemistry, vol. 255, No. 22, 1980, pp. 11011-11016.
A. R. Dunn et al., "A Novel Method to Map Transcripts: Evidence for Homology between an Adenovirus mRNA and Discrete Multiple Regions of the Viral Genome", Cell, vol. 12, Sep. 1977, pp. 23-36.
G. Wengler et al.,"A Study of Nucleotide Sequence Homology Between the Nucleic Acids of Different Alphaviruses", Virology, vol. 78, No. 1, 1977, pp. 124-134.
J. M. Coffin et al., "Structure of the Genome of Moloney Murine Leukemia Virus: A Terminally Redundant Sequence" Cell, vol. 13, No. 4, Apr. 1978, pp. 761-773.
A. Palva et al., "Laboratory Methods, Quantification of α-Amylase mRNA in *Bacillus subtilis* by Nucleic Acid Sandwich with Hybridization", DNA, vol. 7, No. 2, 1988, pp. 135-142.
R. Drmanic et al., "Sequencing of Megabase Plus DNA by Hybridization: Theory of the Method", abstract presented at Cold Spring Harbor Symposium on Gene Mapping and Sequencing, Apr. 27-May 1, 1988, Cold Spring Harbor, NY.
R. Drmanac et al., "Sequencing by Hybridization, Theory of the Method", poster presented at Cold Spring Harbor Symposium on Gene Mapping and Sequencing, Apr. 27-May 1, 1988, Cold Spring Harbor, NY.

I. Labat, "Subfragments as an informative characteristic of the DNA molecule—computer simulation", Search Report, Labat Thesis, (and English translation), 1988.
R. Frank et al., "Simultaneous Synthesis and Biological Applications of DNA Fragments: An Efficient and Complete Methodology", Methods in Enzymology, vol. 154, No. 13, 1987, pp. 221-251.
R. Frank et al., "A new general approach for the simultaneous chemical synthesis of large number of oligonucleotides: segmental solid supports", Nucleic Acids Research, vol. 11, No. 13, 1983, pp. 4365-4377.
A. R. Brautigam et al., "Rapid Typing of Herpes Simplex Virus Isolates by Deoxyribonucleic Acid: Deoxyribonucleic Acid Hybridization", Journal of Clinical Microbiology, vol. 12, No. 2, Aug. 1980, pp. 226-234.
R. K. Saiki et al., "Analysis of Enzymatically Amplified β-globin and HLA-DQα DNA with Allele-Specific Oligonucleotide Probes", Nature, vol. 324, Nov. 1986, pp. 163-166.
A. Rosenthal et al., "Solid-phase methods for sequencing of nucleic acids I. Simultaneous sequencing of different eligodeoxyribonucleotides using a new, mechanically stable anion-exchange paper", Nucleic Acid Research, vol. 13, No. 4, Nov. 4, 1985, pp. 1173-1184.
B. Lewin, Ed., "Genes", Third Edition, 1987, pp. 360-362, John Wiley & Sons, NY, NY.
R. B. Wallace et al., "Hybridization of Synthetic Oligodeoxyribonucleotides to $O_x174$ DNA: The Effect of Single Base Pair Mismatch", Nucleic Acids Research, vol. 6, No. 11, 1979, pp. 3543-3557.
G. Beltz et al., "Isolation of Multigene Families and Determination of Homologies by Filter Hybridization Methods", Methods in Enzymology, vol. 100, No. 19, 1983, pp. 266-285.
Doklady Biochemistry, Proceedings of the Academy of Sciences of the USSR, Biochemistry Section, Russian Original, vol. 303, No. 1-6, Nov.-Dec. 1988, pp. 355-452 and Translation from Russian, Consultants Bureau, New York, Plenum Publishing Corporation, 1989, pp. 436-438.
F. C. Kafatos et al., "Determination of Nucleic Acid Sequence Homologies and Relative Concentrations by a dot Hybridization Procedure", Nucleic Acids Research, vol. 7, No. 6, 1979, pp. 1541-1552.
R. J. Lipshutz et al., "Using Oligonucleotide Probe Arrays to Access Genetic Diversity", BioTechniques, vol. 19, No. 3, 1995, pp. 442-447.
T. R. Gingeras et al., "Hybridization Properties of Immobilized Nucleic Acid", Nucleic Acids Research, vol. 15, No. 13, 1987, pp. 5373-5390.
P.T. Gilham, "The Synthesis of Polynucleotide-Celluloses and Their use in the Fractionation of Polynucleotides", J. Am. Chem. Soc., vol. 86, Nov. 20, 1964, pp. 4982-4985.
H. M. Geysen et al., "Strategies for Epitope Analysis using Peptide Synthesis", Journal of Immunological Methods, vol. 102, 1987, pp. 259-274.
G. M. Church et al., "Genomic Sequencing", Proc. Natl. Acad. Sci., vol. 81(7), Apr. 1984, pp. 1991-1995.
V. J. Kidd et al., "$α_1$-Antitrypsin Deficiency Detection by Direct Analysis of the Mutation in the Gene", Nature, vol. 304, Jul. 1983, pp. 230-234.
P. Masinkowski et al.,"Cloning f cDNA Sequences of Hormone-regulated Gene from the MCF-7 Human Breast Cancer Cell Line", Nucleic Acids Research, vol. 10, No. 24, 1982, pp. 7895-7903.
G. K. Sim et al., "Use of a cDNA Library for Studies on Evolution and Development Expression of the Chorion Multigene Families", Cell, vol. 18, No. 4, Dec. 1979, pp. 1303-1316.
Margaret L. M. Anderson et al., "Quantitative Filter Hybridisation", Nucleic Action Hybridisation, A Practical Approach, 1985, pp. 73-111, IRL Press, Washington, D.C.
W. Bains et al., "A Novel Method for Nucleic Acid Sequence Determination", J. Theor. Biol., vol. 135, 1988, pp. 303-307.
U. B. Voss et al., "The Immobilization of Oligonucleotides and Their Hybridization Properties", Biochemical Society Transactions, vol. 16, 1988, pp. 216-217.

Ghosh et al., "Covalent Attachment of oligonucleotides to Solid Supports", Nucleic Acids Research, vol. 15, No. 13, 1987, pp. 5353-5372.
Federation Proceedings, vol. 43, No. 7, May 4, 1984, Abstract 3669.
T. Maniatis et al., "Molecular Cloning", A Laboratory Manual, Cold Spring Harbor Laboratory, 1982, p. 282, Cold Spring Harbor, NY.
C. R. Cantor et al., "Report on the Sequencing by Hybridization Workshop", Genomics, vol. 13, 1992, pp. 1378-1383.
T. L. Bugawan et al., "Rapid HLA-DLB Typing Using Enzymatically Amplified DNA and Nonradioactive Sequencing-Specific Oligonucleotide Probes", Immunogenetics, vol. 32, 1990, pp. 231-241.
Global Technology Group, Flier for PA Consulting Group, 1988.
Stephen P. A. Fodor et al., "Light-Directed, Spatially Addressable Parallel Chemical Synthesis", Science, vol. 251, Feb. 15, 1991, pp. 767-773.
U. Maskos et al., "A Study of Oligonucleotide Reassociation using Large Arrays of Oligonucleotides Synthesised on a Glass Support", Nucleic Acids Research, vol. 21, No. 20, 1992, pp. 4663-4669.
U. Maskos et al., "Parallel Analysis of Oligodeoxyribonucleotide (Oligonucleotide) Interactions. I. Analysis of Factors Influencing Oligonucleotide Duplex Formation", Nucleic Acids Research, vol. 20, No. 7, 1992, pp. 1675-1678.
J. C. Williams et al., "Studies of Oligonucleotide Interactions by Hybridisation to Arrays: The Influence of Dangling Ends on Duplex Yield", Nucleic Acids Research, vol. 22, No. 8, 1994, pp. 1365-1367.
E. M. Southern et al., Arrays of Complementary Oligonucleotides for Analysing the Hybridisation Behaviour of Nucleic Acids, Nucleic Acids Research, vol. 22, No. 8, 1994, pp. 1368-1373.
M. S. Shchepinov et al.,"Steric Factors Influencing Hybridisation of Nucleic Acids to Oligonucleotide Arrays", Nucleic Acids Research, vol. 25, No. 6, 1997, pp. 1155-1161.
S. C Case-Green et al.,"Studies on the Base Pairing Properties of Deoxyinosine by Solid Phase Hybridisation to Oligonucleotides", Nucleic Acids Research, vol. 22, No. 2, 1994, pp. 131-136.
U. Maskos et al., "A Novel Method for the Parallel Analysis of Multiple Mutations in Multiple Samples", Nucleic Acids Research, vol. 21, No. 9, 1993, 2269-2270.
M. J. Kozal et al., "Extensive Polymorphisms Observed in HIV-1 Clade B Protease Gene Using High-Density Oligonucleotide Arrays", Nature Medicine, vol. 2, No. 7, Jul. 1996, pp. 753-759.
M. Chee et al., "Accessing Genetic Information with High-Density DNA Arrays", Science, vol. 274, Oct. 1996, pp. 610-614.
Kirk -Othmer, Encyclopedia of Chemical Technology, Third Edition, vol. 3, pp. 487-491, 1978.
Kirk-Othmer, Encyclopedia of Chemical Technology, Third Edition, vol. 15, p. 224, 1981.
R. Polsky-Cynkin et al., Use of DNA Immobilized on Plastic and Agarose Supports to Detect DNA by Sandwich Hybridization, Clinical Chemistry, vol. 31, No. 9, 1985, pp. 1438-1443.
J. Welsh et al.,"Protein-DNA Cross-Linking" TIBS, vol. 9, Dec. 1984, pp. 505-508.
G. H. Parsons, Jr., "Antibody-Coated Plastic Tubes in Radioimmunoassay", Meth., Enzymol., vol. 73, 1973, pp. 224-238.
Southern et al., Genomics, "Analyzing and Comprising Nucleic Acid Sequences by Hybridization to Arrays of Oligonucleotides", vol. 13, 1992, pp. 1008-1017.
Webster's Third New International Dictionary, G & C Merriam Company, Publishers, Springfield, Massachusetts, USA, 1966, pages with the definitions of the terms "solid" and "sheet".
The American Heritage Dictionary, Second College Edition, Houghton Mifflin Company, Boston, Massachusetts, 1991, page with the definition of the term "smooth".
The Dictionary of Ceramic Science and Engineering, Plenum Press, New York, NY, 1984—definition of "smooth glass".
Academic Press Dictionary of Science and Technology, San Diego, CA , 1992—definition of "smooth".
S. F. Wolf et al., "Rapid Hybridization Kinetics of DNA Attached to Submicron Latex Particles", Nucleic Acids Research, vol. 15, No. 7, 1987, pp. 2911-2926.
J. N. Kremsky et al., "Immobilization of DNA via Oligonucleotides Containing an Aldehyde or Carboxylic Acid Group at the 5' Terminus", Nucleic Acids Research, vol. 15, No. 7, 1987, pp. 2891-2909.
Letter to Simon Kiddie from Dr. Renzo Malvano, Nov. 2002.
Letter to Simon Kiddie from Dr. Gian Carlo Zucchelli, Nov. 2002.
Declaration of Professor Alberto Albertini, Nov. 2002.
Declaration of Dr. Gianni Messeri, Nov. 2002.
Second Statement of Professor Roger Ekins, Jan. 2003.
Slides used in Professor Ekins' lecture at the International Biotech RIA '88 Conference in Florence on Apr. 11, 1988.
Lev. D. Gelb and K.E. Gubbins, "Characterization of Porous Glasses by Adsorption: Models, Simulations and Data Inversion", Fundamentals of Adsorption, vol. 6, 1999, pp. 551-556.
Pharmacia Catalogue 1998, page describing Hybond-NX.
Translation of EP A 0197266 filed for UK national validation, 1991.
E. M. Southern, Award Molecular Bioanalytics 2004, Biography.
Award Molecular Bioanalytics 2004.
Bio Array News, vol. 1, No. 1, Jun. 1, 2001, pp. 1-10.
News Events, Journal of Biomolecular Techniques, vol. 15, 2004, pp. 152-153.
Decision of Oct. 12, 2005 by the Boards of Appeal of the European Patent Office with respect to EP 0 373 203 B1.
Saiki R.K. et al. in Proceedings of the National Academy of Science U.S.A. vol. 86, pp. 6230-6234 entitled Genetic analysis of amplified DNA with immobilized sequence-specific oligonucleotide probes.
Request for Reexam of USP 6,054,270, Office Action dated Aug. 24, 2007 and Applicant's Response in Ex parte Reexamination Control U.S. Appl. No. 90/008,428.
Memorandum Opinion by U.S. District Court in *Oxford Gene Technology v. Mergen Limited* et al., Civil Action No. 02-1695, Sep. 29, 2004.
J. Kremsky et al., "Immobilization of DNA via oligonucleotides containing an aldehyde or carboxylic acid group at the 5' terminus", Journal IRL Press Limited, Oxford, England, vol. 15, Issue 7, pp. 2891-2909, 1987.
A. F. Cook et al., "Synthesis and Hybridization of a series of biotinylated oligonucleotides", Journal IRL Press Limited, Oxford, England, vol. 16, Issue 9, pp. 4077-4095, 1988.
G. K. Sim et al., "Use of a cDNA library for studies on evolution and developmental expression of the chorion multigene families", Journal MIT (US), vol. 18, pp. 1303-1316, 1979.
R. Polsky-Cynkin et al., "Use of DNA immobilized on plastic and agarose supports to detect DNA by sandwich hybridization", Journal Clinical Chemistry (US), vol. 31, Issue 9, pp. 1438-1443, 1985.
Renewed Request for Reexam of USP 6,054,270 in Ex parte Reexamination Contol U.S. Appl. No. 90/010,020.
R. K. Saiki et al., "Genetic analysis of amplified DNA with immobilized sequence-specific oligonucleotide probes", PNAS, U.S.A., vol. 86, pp. 6230-6234, 1989.
I. Labat et al., Research Report for the University of Belgrade College of Natural Sciences and Mathematics, 1988 (Serb-Croat and partial English translation).
Request for Reexamination of USP 6,054,270 and PTO Order granting Reexam in Ex parte Reexamination Control U.S. Appl. No. 90/008,830.
Declaration of Edwin Southern, Jan. 16, 1989.
Declaration of Edwin Southern, Dec. 7, 2001.
Declaration of Glen McGall, Jan. 13, 1999.
Declaration of Calvin Quade, Jan. 9, 1999.
Bains et al., "A novel method for nucleic acid sequence determination"; J. Theor. Biol., 1988, vol. 135, pp. 303-307.
Urdea et al., "A novel method for the rapid detection of specific nucleotide sequences in crude biological samples without blotting or radioactivity; application to the analysis of hepatitis B virus in human serum", Gene, 1987, vol. 61, pp. 253-264.
Request for Reexam of USP 5,700,637, and PTO Order granting Reexam in Ex parte Reexamination Control U.S. Appl. No. 90/008,844.
W. Bannwarth et al., "A system for the simultaneous chemical synthesis of different DNA fragments on solid support", DNA, Oct. 1986, vol. 5, No. 5, pp. 413-419.
Applied Biosystems Model 380B DNA Synthesizer Version 1.0 User's Manual (the Synthesizer manual).

Markman ruling from *Oxford Gene Technology* v. *Affymetrix Corporation*.

Request for Reexam of USP 5,700,637 and Office Action issued Oct. 24, 2007 in Ex parte Reexamination Control U.S. Appl. No. 90/008,429.

A. F. Cook et al., "Synthesis and hybridization of a series of biotinylated oligonucleotides", Nucleic Acids Research, vol. 16, No. 9, pp. 4077-4095, 1988.

M. S. Urdea et al., "A comparison of non-radioisotopic hybridization assay methods using fluorescent, chemiluminescent and enzyme labeled synthetic oligodeoxyribonucleotide probes", Nucleic Acids Research, vol. 16, No. 11, pp. 4937-4956, 1988.

Declaratory Judgment Action filed by Autogenomics against Oxford Gene Technology Limited in the United States District Court for the Central District of California against USP 6,054,270.

* cited by examiner

ANALYSING POLYNUCLEOTIDE SEQUENCES

This application is a divisional application of Ser. No. 09/422,803 filed Oct. 22, 1999, now abandoned which is a divisional application of Ser. No. 08/925,676 filed Sep. 9, 1997, now U.S. Pat. No. 6,054,270 which is a divisional of application Ser. No. 08/230,012 filed Apr. 19, 1994, now U.S. Pat. No. 5,700,637, which is a continuation of abandoned application Ser. No. 08/695,682 filed May 3, 1991, which is a continuation-in-part of abandoned application Ser. No. 07/573,317 filed Sep. 28, 1990, which is a 371 of international application PCT/GB89/00460 filed May 2, 1989.

1. INTRODUCTION

Three methods dominate molecular analysis of nucleic acid sequences: gel electrophoresis of restriction fragments, molecular hybridisation, and the rapid DNA sequencing methods. These three methods have a very wide range of applications in biology, both in basic studies, and in the applied areas of the subject such as medicine and agriculture. Some idea of the scale on which the methods are now used is given by the rate of accumulation of DNA sequences, which is now well over one million base pairs a year. However, powerful as they are, they have their limitations. The restriction fragment and hybridisation methods give a coarse analysis of an extensive region, but are rapid; sequence analysis gives the ultimate resolution, but it is slow, analysing only a short stretch at a time. There is a need for methods which are faster than the present methods, and in particular for methods which cover a large amount of sequence in each analysis.

This invention provides a new approach which produces both a fingerprint and a partial or complete sequence in a single analysis, and may be used directly with complex DNAs and populations of RNA without the need for cloning.

In one aspect the invention provides apparatus for analysing a polynucleotide sequence, comprising a support and attached to a surface thereof an array of the whole or a chosen part of a complete set of oligo nucleotides of chosen lengths, the different oligonucleotides occupying separate cells of the array and being capable of taking part in hybridisation reactions. For studying differences between polynucleotide sequences, the invention provides in another aspect apparatus comprising a support and attached to a surface thereof an array of the whole or a chosen part of a complete set of oligonucleotides of chosen lengths comprising the polynucleotide sequences, the different oligonucleotides occupying separate cells of the array and being capable of taking part in hybridisation reactions.

In another aspect, the invention provides a method of analysing a polynucleotide sequence, by the use of a support to the surface of which is attached an array of the whole or a chosen part of a complete set of oligo nucleotides of chosen lengths, the different oligonucleotides occupying separate cells of the array, which method comprises labelling the polynucleotide sequence or fragments thereof to form labelled material, applying the labelled material under hybridisation conditions to the array, and observing the location of the label on the surface associated with particular members of the set of oligonucleotides.

The idea of the invention is thus to provide a structured array of the whole or a chosen part of a complete set of oligonucleotides of one or several chosen lengths. The array, which may be laid out on a supporting film or glass plate, forms the target for a hybridisation reaction. The chosen conditions of hybridisation and the length of the oligonucleotides must at all events be sufficient for the available equipment to be able to discriminate between exactly matched and mismatched oligonucleotides. In the hybridisation reaction, the array is explored by a labelled probe, which may comprise oligomers of the chosen length or longer polynucleotide sequences or fragments, and whose nature depends on the particular application. For example, the probe may comprise labelled sequences amplified from genomic DNA by the polymerase chain reaction or a mRNA population, or a complete set of oligonucleotides from a complex sequence such as an entire genome. The end result is a set of filled cells corresponding to the oligonucleotides present in the analysed sequence, and a set of "empty" sites corresponding to the sequences which are absent in the analysed sequence. The pattern produces a fingerprint representing all of the sequence analysed. In addition, it is possible to assemble most or all of the sequence analysed if an oligonucleotide length is chosen such that most or all oligonucleotide sequences occur only once.

The number, the length and the sequences of the oligonucleotides present in the array "lookup table" also depend on the application. The array may include all possible oligonucleotides of the chosen length, as would be required if there was no sequence information on the sequence to be analysed. In this case, the preferred length of oligonucleotide used depends on the length of the sequence to be analysed, and is such that there is likely to be only one copy of any particular oligomer in the sequence to be analysed. Such arrays are large. If there is any information available on the sequence to be analysed, the array may be a selected subset. For the analysis of a sequence which is known, the size of the array is of the same order as length of the sequence, and for many applications, such as the analysis of a gene for mutations, it can be quite small. These factors are discussed in detail in what follows.

2. OLIGONUCLEOTIDES AS SEQUENCE PROBES

Oligonucleotides form base paired duplexes with oligonucleotides which have the complementary base sequence. The stability of the duplex is dependent on the length of the oligonucleotides and on base composition. Effects of base composition on duplex stability can be greatly reduced by the presence of high concentrations of quaternary or tertiary amines. However, there is a strong effect of mismatches in the oligonucleotides duplex on the thermal stability of the hybrid, and it is this which makes the technique of hybridisation with oligonucleotides such a powerful method for the analysis of mutations, and for the selection of specific sequences for amplification by DNA polymerase chain reaction. The position of the mismatch affects the degree of destabilisation. Mismatches in the cetre of the duplex may cause a lowering of the Tm by 10° C. compared with 1° C. for a terminal mismatch. There is then a range of discriminating power depending on the position of mismatch, which has implications for the method described here. There are ways of improving the discriminating power, for example by carrying out hybridisation close to the Tm of the duplex to reduce the rate of formation of mismatching duplexes, and by increasing the length of oligonucleotide beyond what is required for unique representation. A way of doing this systematically is discussed.

3. ANALYSIS OF A PREDETERMINED SEQUENCE

One of the most power uses of oligonucleotide probes has been in the detection of single base changes in human genes. The first example was the detection of the single base change in the betaglobin gene which leads to sickle cell disease. There is a need to extend this approach to genes in which there may be a number of different mutations leading to the same phenotype, for example the DMD gene and the HPRT gene, and to find an efficient way of scanning the human genome for mutations in regions which have been shown by linkage analysis to contain a disease locus for example Huntington's disease and Cystic Fibrosis. Any known sequence can be presented completely as a set of overlapping oligonucleotides. The size of the set is N s+1=N, where N is the length of the sequence and s is the length of an oligomer. A gene of 1 kb for example, may be divided into an overlapping set of around one thousand oligonucleotides of any chosen length. An array constructed with each of these oligonucleotides in a separate cell can be used as a multiple hybridisation probe to examine the homologous sequence in any context, a single-copy gene in the human genome or a messenger RNA among a mixed RNA population, for example. The length s may be chosen such that there is only a small probability that any oligomer in the sequence is represented elsewhere in the sequence to be analysed. This can be estimated from the expression given in the section discussing statistics below. For a less complete analysis it would be possible to reduce the size of the array e.g. by a factor of up to 5 by representing the sequence in a partly or non-overlapping set. The advantage of using a completely overlapping set is that it provides a more precise location of any sequence difference, as the mismatch will scan in $\underline{s}$ consecutive oligonucleotides.

4. ANALYSIS OF UNDETERMINED SEQUENCE

The genomes of all free living organisms are larger than a million base pairs and none has yet been sequenced completely. Restriction site mapping reveals only a small part of the sequence, and can detect only a small portion of mutations when used to compare two genomes. More efficient methods for analysing complex sequences are needed to bring the full power of molecular genetics to bear on the many biological problems for which there is no direct access to the gene or genes involved. In many cases, the full sequence of the nucleic acids need not be determined; the important sequences are those which differ between two nucleic acids. To give three examples: the DNA sequences which are different between a wild type organism and one which carries a mutant can lead the way to isolation of the relevant gene; similarly, the sequence differences between a cancer cell and its normal counterpart can reveal the cause of transformation; and the RNA sequences which differ between two cell types point to the functions which distinguish them. These problems can be opened to molecular analysis by a method which identifies sequence differences. Using the approach outlined here, such differences can be revealed by hybridising the two nucleic acids, for example the genomic DNA and the two genotypes, or the mRNA populations of two cell types to an array of oligonucleotides which represent all possible sequences. Positions in the array which are occupied by one sequence but not by the other show differences in two sequences. This gives the sequence information needed to synthesize probes which can then be used to isolate clones of the sequence involved.

4.1 Assembling the Sequence Information

Sequences can be reconstructed by examining the result of hybridisation to an array. Any oligonucleotide of length s from within a long sequence, overlaps with two others over a length s-1. Starting from each positive oligonucleotide, the array may be examined for the four oligonucleotides to the left and the four to the right that can overlap with one base displacement. If only one of these four oligonucleotides is found to be positive to the right, then the overlap and the additional base to the right determine s bases in the unknown sequence. The process is repeated in both directions, seeking unique matches with other positive oligonucleotides in the array. Each unique match adds a base to the reconstructed sequence.

4.2 Some Statistics

Any sequence of length N can be broken down to a set of ~N overlapping sequences s base pairs in length. (For double stranded nucleic acids, the sequence complexity of a sequence of N base pairs is 2N, because the two strands have different sequences, but for the present purpose, this factor of two is not significant). For oligonucleotides of length s, there are $4^s$ different sequence combinations. How big should s be to ensure that most oligonucleotides will be represented only once in the sequence to be analysed, of complexity N? For a random sequence the expected number of s-mers which will be present in more than one copy is $$\mu_{>1} \approx 4'(1-e^{-\lambda}(1+\lambda))$$

where $$\lambda = (N-s+1)/4'$$

For practical reasons it is also useful to know how many sequences are related to any given s-mer by a single base change. Each position can be substituted by one of three bases, there are therefore 3s sequences related to an individual s-mer by a single base change; and the probability that any s-mer is a sequence of N bases is related to any other s-mer in that sequence allowing one substitution is $3s \times N/4^s$. The relative signals of matched and mismatched sequences will then depend on how good the hybridisation conditions are in distinguishing a perfect match from one which differ by a single base. (If $4^s$ is an order of magnitude greater than N, there should only be a few, 3s/10, related to any oligonucleotide by one base change.) The indications are that the yield of hybrid from the mismatched sequence is a fraction of that formed by the perfect duplex.

For what follows, it is assumed that conditions can be found which allow oligonucleotides which have complements in the probe to be distinguished from those which do not.

4.3 Array Format, Construction and Site

To form an idea of the scale of the arrays needed to analyse sequences of different complexity it is convenient to think of the array as a square matrix. All sequences of a given length can be represented just once in a matrix constructed by drawing four rows representing the four bases, followed by four similar columns. This produces 4×4 matrix in which each of the 16 squares represents one of the 16 doublets. Four similar matrixes, but one quarter the size are then drawn within each of the original squares. This produces a 16×16 matrix containing all 256 tetranucleotide sequences. Repeating this process produces a matrix of any chosen depth, s, with a number of cells equal to $4^s$. As discussed above, the choice of s is of great importance, as it determines the complexity of the sequence representation. As discussed below, s also determines the size of the matrix constructed, which must be very big for complex genomes. Finally, the length of the oligonucleotides determines the hybridisation conditions and their discriminating power as hybridisation probes.

| s | $4^S$ | Genomes | Size of Matrix (pixel = 100 µm; | Number of Sheets of Film |
|---|---|---|---|---|
| 8 | 65536 | $4^S \times 10$ | | |
| 9 | 262144 | | | |
| 10 | $1.0 \times 10^6$ | cosmid | 100 mm | 1 |
| 11 | $4.2 \times 10^6$ | | | |
| 12 | $1.7 \times 10^7$ | | | |
| 13 | $6.7 \times 10^7$ | E. coli | | |
| 14 | $2.6 \times 10^8$ | yeast | 1.6 m | 9 |
| 15 | $1.1 \times 10^9$ | | | |
| 16 | $4.2 \times 10^9$ | | | |
| 17 | $1.7 \times 10^{10}$ | | | |
| 18 | $6.7 \times 10^{10}$ | human | 25 m | 2,500 |
| 19 | $2.7 \times 10^{11}$ | | | |
| 20 | $1.1 \times 10^{12}$ | | 100 m | |

The table shows the expected scale of the arrays needed to perform the first analysis of a few genomes. The examples are chosen because they are genomes which have either been sequenced by conventional procedures—the cosmid scale—, are in the process of being sequenced—the *E. coli* scale—, or for which there has been considerable discussion of the magnitude of the problem—the human scale. the table shows that the expected scale of the matrix approach is only a small fraction of the conventional approach. This is readily seen in the area of X-ray film that would be consumed. It is also evident that the time taken for the analysis would be only a small fraction of that needed for gel methods. The "Genomes" column shows the length of random sequence which would fill about 5% of cells in the matrix. This has been determined to be the optimum condition for the first step in the sequencing strategy discussed below. At this size, a high proportion of the positive signals would represent single occurrences of each oligomer, the conditions needed to compare two genomes for sequence differences.

5. REFINEMENT OF AN INCOMPLETE SEQUENCE

Reconstruction of a complex sequence produces a result in which the reconstructed sequence is interrupted at any point where an oligomer that is repeated in the sequence occurs. Some repeats are present as components of long repeating structures which form part of the structural organisation of the DNA, dispersed and tandum repeats in human DNA for example. But when the length of oligonucleotide used in the matrix is smaller than that needed to give totally unique sequence representation, repeats occur by chance. Such repeats are likely to be isolated. That is, the sequences surrounding the repeated oligomer are unrelated to each other. The gaps caused by these repeats can be removed by extending the sequence to longer oligomers. In principle, those sequences shown to be repeated by the first analysis, using an array representation of all possible oligomers, could be resynthesised with an extension at each end. For each repeated oligomer, there would be 4×4=16 oligomers in the new matrix. The hybridisation analysis would now be repeated until the sequence was complete. In practice, because the results of a positive signal in the hybridisation may be ambiguous, it may be better to adopt a refinement of the first result by extending all sequences which did not give a clear negative result in the first analysis. An advantage of this approach is that extending the sequence brings mismatches which are close to the ends in the shorter oligomer, closer to the centre in the extended oligomer, increasing the discriminatory power of duplex formation.

5.1 A Hypothetical Analysis of the Sequence of Bacteriophage λ DNA

Lambda phage DNA is 48,502 base pairs long. Its sequence has been completely determined, we have treated one strand of this as a test case in a computer simulation of the analysis. The table shows that the appropriate size of oligomer to use for a sequence of this complexity is the 10-mer. With a matrix of 10-mers, the size of 1024 lines square. After "hybridisation" of the lambda 10-mers in the computer, 46,377 cells were positive, 1957 had double occurrences, 75 triple occurrences, and three quadruple occurrences. These 46,377 positive cells represented known sequences, determined from their position in the matrix. Each was extended by four×one base at the 3' end and four×one case at the 5', end to give 16×46,377=742,032 cells. This extended set reduced the number of double occurrences to 161, a further 16-fold extension brought the number down to 10, and one more provided a completely overlapped result. Of course, the same end result of a fully overlapped sequence could be achieved starting with a $4^{16}$ matrix, but the matrix would be 4000 times bigger than the matrix needed to represent all 10-mers, and most of the sequence represented on it would be redundant.

5.2 Laying Down the Matrix

The method described here envisages that the matrix will be produced by synthesising oligonucleotides in the cells of an array by laying down the precursors for the four bases in a predetermined pattern, an example of which is described above. Automatic equipment for applying the precursors has yet to be developed, but there are obvious possibilities; it should not be difficult to adapt a pen plotter or other computer-controlled printing device to the purpose. The smaller the pixel size of the array the better, as complex genomes need very large numbers of cells. However, there are limits to how small these can be made. 100 microns would be a fairly comfortable upper limit, but could probably not be achieved on paper for reasons of texture and diffusion. On a smooth impermeable surface, such as glass, it may be possible to achieve a resolution of around 10 microns, for example by using a laser typesetter to preform a solvent repellant grid, and building the oligonucleotides in the exposed regions. One attractive possibility, which allows adaptation of present techniques of oligonucleotide synthesis, is to sinter microporous glass in microscopic patches onto the surface of a glass plate. Laying down very large number of lines or dots could take a long time, if the printing mechanism were slow. However, a low cost ink-jet printer can print at speeds of about 10,000 spots per second. With this sort of speed, $10^8$ spots could be printed in about three hours.

5.3 Oligonucleotide Synthesis

There are several methods of synthesising oligonucleotides. Most methods in current use attach the nucleotides to a solid support of controlled pore size glass (CPG) and are suitable for adaptation to synthesis on a glass surface. Although we know of no description of the direct use of oligonucleotides as hybridisation probes while still attached to the matrix on which they were synthesised, there are reports of the use oligonucleotides as hybridisation probes on solid supports to which they were attached after synthesis. PCT Application WO 85/01051 describes a method for synthesising oligonucleotides tethered to a CPG column. In an experiment performed by us, CPG was used as the support in an Applied Bio-systems oligonucleotide synthesiser to synthesise a 13-mer complementary to the left hand cos site of phage lambda. The coupling steps were all close to theoretical yield. The first base was stably attached to the support medium through all the synthesis and deprotection steps by a covalent link.

5.4 Analysing Several Sequences Simultaneously

The method of this invention can be used to analyse several polynucleotide sequences simultaneously. To achieve this, the oligonucleotides may be attached to the support in the form of (for example) horizontal stripes. A technique for doing this is described in Example 3 below. Each DNA sample to be analysed is labelled and applied to the surface carrying the oligonucleotides in the form of a stripe (e.g. vertical) orthogonal to the oligonucleotide stripes of the array. Hybridisation is seen at the intersections between oligonucleotide stripes and stripes of test sequence where there is homology between them.

Where sequence variations are known, an advantage of using this technique is that many different mutations can be probed simultaneously by laying down stripes corresponding to each allelic variant. With a density of one oligonucleotide per mm, and one "individual" per 5 mm, it should be possible to analyse 2000 loci on a plate 100 mm square. Such a high density of information, where the oligonucleotides do identify specific alleles, is not available by other techniques.

6. PROBES, HYBRIDISATION AND DETECTION

The yield of oligonucleotides synthesised on microporous glass is about 30 µmol/g. A patch of this material 1 micron thick by 10 microns square would hold ~$3 \times 10^{-12}$ µmol equivalent to about 2 g of human DNA. The hybridisation reaction could therefore be carried out with a very large excess of the bound oligonucleotides over that in the probe. So it should be possible to design a system capable of distinguishing between hybridisation involving single and multiple occurrances of the probe sequence, as yield will be proportional to concentration at all stages in the reaction.

The polynucleotide sequence to be analysed may be of DNA or RNA. To prepare the probe, the polynucleotide may be degraded to form fragments. Preferably it is degraded by a method which is as random as possible, to an average length around the chosen length s of the oligonucleotides on the support, the oligomers of exact length s selected by electrophoresis on a sequencing gel. The probe is then labelled. For example, oligonucleotides of length s may be end labelled. If labelled with $^{32}P$, the radioactive yield of any individual s-mer even from total human DNA could be more than $10^4$ dpm/mg of total DNA. For detection, only a small fraction of this is needed in a patch 10-100 microns square. This allows hybridisation conditions to be chosen to be close to the Tm of duplexes, which decreases the yield of hybrid and decreases the rate of formation, but increases the discriminating power. Since the bound oligonucleotide is in excess, signal need not be a problem even working close to equilibrium.

Hybridisation conditions can be chosen to be those known to be suitable in standard procedures used to hybridise to filters, but establishing optimum conditions is important. in particular, temperature needs to be controlled closely, preferably to better than ±0.5° C. Particularly when the chosen length of the oligonucleotide is small, the analysis needs to be able to distinguish between slight differences of rate and/or extent of hybridisation. The equipment may need to be programmed for differences in base composition between different oligonucleotides. In constructing the array, it may be preferable to partition this into sub-matrices with similar base compositions. This may make it easier to define the Tm which may differ slightly according to the base composition.

The choice of hybridisation solvent is significant. When 1M NaCl is used, G:C base pairs are more stable than A:T base pairs. Double stranded oligonucleotides with a high G+C content have a higher Tm than corresponding oligonucleotides with a high A+T content. This discrepancy can be compensated in various ways: the amount of oligonucleotide laid down on the surface of the support can be varied depending on its nucleotide composition; or the computer used to analyse the data can be programmed to compensate for variations in nucleotide composition. A preferred method, which can be used either instead of or in addition to those already mentioned, is to use a chaotropic hybridisation solvent, for example a quaternary or tertiary amine as mentioned above. Tetramethylammoniumchloride (TMACl) has proved particularly suitable, at concentrations in the range 2 M to 5.5 M. At TMACl concentrations around 3.5 M to 4 M, the $T_m$ dependence on nucleotide composition is greatly reduced.

The nature of the hybridisation salt used also has a major effect on the overall hybridisation yield. Thus, the use of TMACl at concentrations up to 5 M can increase the overall hybridisation yield by a factor of 30 or more (the exact figure depending to some extent on nucleotide composition) in comparison with hybridisation using 1M NaCl. Manifestly, this has important implications; for example the amount of probe material that needs to be used to achieve a given signal can be much lower.

Autoradiography, especially with $^{32}P$ causes image degradation which may be a limiting factor determining resolution; the limit for silver halide films is around 25 microns. Obviously some direct detection system would be better. Fluorescent probes are envisaged; given the high concentration of the target oligonucleotides, the low sensitivity of fluorescence may not be a problem.

We have considerable experience of scanning auto-radiographic images with a digitising scanner. Our percent design is capable of resolution down to 25 microns, which could readily be extended down to less than present application, depending on the quality of the hybridisation reaction, and how good it is at distinguishing absence of a sequence from the presence of one or more. Devices for measuring astronomical plates have an accuracy around 1 µ. Scan speeds are such that a matrix of several million cells can be scanned in a few minutes. Software for the analysis of the data is straightforward, though the large data sets need a fast computer.

Experiments presented below demonstrate the feasibility of the claims.

Commercially available microscope slides (BDH Super Premium 76×26×1 mm) were used as supports. These were derivatised with a long aliphatic linker that can withstand the conditions used for the deprotection of the aromatic heterocyclic bases, i.e. 30% $NH_3$ at 55° for 10 hours. The linker, bearing a hydroxyl group which serves as a starting point for the subsequent oligonucleotide, is synthesized in two steps. The slides are first treated with a 25% solution of 3-glycidoxypropyltriethoxysilane in xylene containing several drops of Hunig's base as a catalyst. The reaction is carried out in a staining jar, fitted with a drying tube, for 20 hours at 90° C. The slides are washed with MeOH, $Et_2O$ and air dried. Then neat hexaethylene glycol and a trace amount of conc. sulphuric acid are added and the mixture kept at 80° C. for 20 hours. The slides are washed with MeOH, $Et_2O$, air dried and stored desiccated at −20° until use. This preparative technique is described in British Patent Application 8822228.6 filed 21 Sep. 1988.

The oligonucleotide synthesis cycle is performed as follows:

The coupling solution is made up fresh for each step by mixing 6 vol. of 0.5 M tetrazole in anhydrous acetonitrile with 5 vol. of a 0.2 M solution of the required betacyanoethylphosphoramidite. Coupling time is three minutes. Oxidation with a 0.1 M solution of $I_2$ in THF/pyridine/$H_2O$ yields a stable phosphotriester bond. Detritylation of the 5' end with 3% trichloroacetic acid in dichloromethane allows further extension of the oligonucleotide chain. There was no capping step since the excess of phosphoramidites used over reactive sites on the slide was large enough to drive the coupling to completion. After the synthesis is completed, the oligonucleotide is deprotected in 30% $NH_3$ for 10 hours at 55°. The chemicals used in the coupling step are moisture-sensitive, and this critical step must be performed under anhydrous conditions in a sealed container, as follows. The shape of the patch to be synthesised was cut out of a sheet of silicone rubber (76×26×0.5 mm) which was sandwiched between a microscope slide, derivatised as described above, and a piece of teflon of the same size and thickness. To this was fitted a short piece of plastic tubing that allowed us to inject and withdraw the coupling solution by syringe and to flush the cavity with Argon. The whole assembly was held together by fold-back paper clips. After coupling the set-up was disassembled and the slide put through the subsequent chemical reactions (oxidation with iodine, and detritylation by treatment with TCA) by dipping it into staining jars.

EXAMPLE 1

As a first example we synthesised the sequences oligo-$dT_{10}$-oligo-$dT_{14}$ on a slide by gradually decreasing the level of the coupling solution in steps 10 to 14. Thus the 10-mer was synthesised on the upper part of the slide, the 14-mer at the bottom and the 11, 12 and 13-mers were in between. We used 10 pmol oligo-$dA_{12}$, labelled at the 5' end with $^{32}P$ by the polynucleotide kinase reaction to a total activity of 1.5 million c.p.m., as a hybridisation probe. Hybridisation was carried out in a perspex (Plexiglas) container made to fit a microscope slide, filled with 1.2 ml of 1 M NaCl in TE, 0.1% SDS, for 5 minutes at 20°. After a short rinse in the same solution without oligonucleotide, we were able to detect more than 2000 c.p.s. with a radiation monitor. An autoradiograph showed that all the counts came from the area where the oligonucleotide had been synthesised, i.e. there was no non-specific binding to the glass or to the region that had been derivatised with the linker only. After partial elution in 0.1 M NaCl differential binding to the target is detectable, i.e. less binding to the shorter than the longer oligo-dT. By gradually heating the slide in the wash solution we determined the $T_m$ (mid-point of transition when 50% eluted) to be 33°. There were no counts detectable after incubation at 39°. The hybridisation and melting was repeated eight times with no diminution of the signal. The result is reproducible. We estimate that at least 5% of the input counts were taken up by the slide at each cycle.

EXAMPLE 2

In order to determine whether we would be able to distinguish between matched and mismatched oligonucleotides we synthesised two sequences 3' CCC GCC GCT GGA (cosL) and 3' CCC GCC TCT GGA, which differ by one base at position 7. All bases except the seventh were added in a rectangular patch. At the seventh base, half of the rectangle was exposed in turn to add the two different bases, in two stripes. Hybridisation of cosR probe oligonucleotide (5' GGG CGG CGA CCT) (kinase labelled with $^{32}P$ to 1.1 million c.p.m., 0.1 M NaCl, TE, 0.1% SDS) was for 5 hours at 32°. The front of the slide showed 100 c.p.s. after rinsing. Autoradiography showed that the annealing occurred only to the part of the slide with the fully complementary oligonucleotide. No signal was detectable on the patch with the mismatched sequence.

EXAMPLE 3

For a further study of the effects of mismatches or shorter sequences on hybridisation behaviour, we constructed two arrays: one (a) of 24 oligonucleotides and the other (b) of 72 oligonucleotides.

These arrays were set out as shown in Table 1(a) and 1(b). The masks used to lay down these arrays were different from those used in previous experiments. Lengths of silicone rubber tubing (1 mm o.d.) were glued with silicone rubber cement to the surface of plain microscope slides, in the form of a "U". Clamping these masks against a derivatised microscope slide produced a cavity into which the coupling solution was introduced through a syringe. In this way only the part of the slide within the cavity came into contact with the phosphoramidite solution. Except in the positions of the mismatched bases, the arrays listed in Table 1 were laid down using a mask which covered most of the width of the slide. Offsetting this mask by 3 mm up or down the derivatised slide in subsequent coupling reactions produced the oligonucleotides truncated at the 3' or 5' ends.

For the introduction of mismatches a mask was used which covered half (for array (a)) or one third (for array (b)) of the width of the first mask. The bases at positions six and seven were laid down in two or three longitudinal stripes. This led to the synthesis of oligonucleotides differing by one base on each half array (array (a)) or third (array (b)) of the slide. In other positions, the sequences differed from the longest sequence by the absence of bases at the ends.

In array (b), there were two columns of sequences between those shown in Table 1(b), in which the sixth and seventh bases were missing in all positions, because the slide was masked in a stripe by the silicone rubber seal. Thus there were a total of 72 different sequences represented on the slide in 90 different positions.

The 19-mer 5' CTC CTG AGG AGA AGT CTG C was used for hybridisation (2 million cpm, 1.2 ml 0.1 M NaCl in TE, 0.1% SDS, 20°).

The washing and elution steps were followed by autoradiography. The slide was kept in the washing solution for 5 minutes at each elution step and then exposed (45 min, intensified). Elution temperatures were 28, 36, 42, 47, 55 and 60° C. respectively.

As indicated in the table, the oligonucleotides showed different melting behaviour. Short oligonucleotides melted before longer ones, and at 55° C., only the perfectly matched 19-mer was stable, all other oligonucleotides had been eluted. Thus the method can differentiate between a 18-mer and a 19-mer which differ only by the absence of one base at the end. Mismatches at the end of the oligonucleotides and at internal sites can all be melted under conditions where the perfect duplex remains.

Thus we are able to use very stringent hybridisation conditions that eliminate annealing to mismatch sequences or to oligonucleotides differing in length by as little as one base. No other method using hybridisation of oligonucleotides bound to the solid supports is so sensitive to the effects of mismatching.

EXAMPLE 4

To test the application of the invention to diagnosis of inherited diseases, we hybridised the array (a), which carries the oligonucleotide sequences specific for the wild type and the sickle cell mutations of the β-globin gene, with a 110 base pair fragment of DNA amplified from the β-globin gene by means of the polymerase chain reaction (PCR). Total DNA from the blood of a normal individual (1 microgram) was amplified by PCR in the presence of appropriate primer oligonucleotides. The resulting 110 base pair fragment was purified by electrophoresis through an agarose gel. After elution, a small sample (ca. 10 picogram) was labelled by using α-$^{32}$P-dCTP (50 microCurie) in a second PCR reaction. This PCR contained only the upstream priming oligonucleotide. After 60 cycles of amplification with an extension time of 9 min. the product was removed from precursors by gel filtration. Gel electrophoresis of the radioactive product showed a major band corresponding in length to the 110 base fragment. One quarter of this product (100,000 c.p.m. in 0.9 M NaCl, TE, 0.1% SDS) was hybridised to the array (a). After 2 hours at 30° ca. 15000 c.p.m. had been taken up. The melting behaviour of the hybrids was followed as described for the 19-mer in example 3, and it was found that the melting behaviour was similar to that of the oligonucleotide. That is to say, the mismatches considerably reduced the melting temperature of the hybrids, and conditions were readily found such that the perfectly matched duplex remained whereas the mismatched duplexes had fully melted.

Thus the invention can be used to analyse long fragments of DNA as well oligonucleotides, and this example shows how it may be used to test nucleic acid sequences for mutations. In particular it shows how it may be applied to the diagnosis of genetic diseases.

EXAMPLE 5

To test an automated system for laying down the precursors, the cosL oligonucleotide was synthesised with 11 of the 12 bases added in the way described above. For the addition of the seventh base, however, the slide was transferred into an Argon filled chamber containing a pen plotter. The pen of the plotter had been replaced by a component, fabricated from Nylon, which had the same shape and dimensions as the pen, but which carried a polytetrafluoroethylene (PTFE) tube, through which chemicals could be delivered to the surface of the glass slide which lay on the bed of the plotter. A microcomputer was used to control the plotter and the syringe pump which delivered the channels. The pen, carrying the delivery tube from the syringe, was moved into position above the slide, the pen was lowered and the pump activated to lay down coupling solution. Filling the pen successively with G, T and A phosphormidite solutions an array of twelve spots was laid down in three groups of four, with three different oligonucleotide sequences. After hybridisation to cosR, as described in Example 2, and autoradiography, signal was seen only over the four spots of perfectly matched oligonucleotides, where the dG had been added.

EXAMPLE 6

This example demonstrates the technique of analysing several DNA sequences simultaneously. Using the technique described in Example 3, a slide was prepared bearing six parallel rows of oligonucleotides running along its length. These comprise duplicate hexadecamer sequences corresponding to antisense sequences of the β-globin wild-type (A), sickle cell (S) and C mutations.

Clinical samples of AC, AS and SS DNA were procured. Three different single-stranded probes of 110 nt length with approx. 70,000 c.p.m. in 100 µl 1 M NaCl, TE pH 7.5, 0.1% SDS, viz AC, AS, and SS DNA were prepared. Radiolabelled nucleotide was included in the standard PCR step yielding a double-stranded labelled fragment. It was made single-stranded with Bacteriophase λ exonuclease that allowed to selectively digest one strand bearing a 5' phosphate. This was made possible by phosphorylating the downstream primer with T4 Polynucleotide kinase and ('cold') ATP prior to PCR. These three probes were applied as three stripes orthogonal to the surface carrying the six oligonucleotide stripes. Incubation was at 30° C. for 2 hours in a moist chamber. The slide was then rinsed at ambient temperature, then 45° C. for 5 minutes and exposed for 4 days with intensification. The genotype of each clinical sample was readily determined from the autoradiographic signals at the points of intersection.

EXAMPLE 7

A plate was prepared whose surface carried an array of all 256 octapurines. That is to say, the array comprised 256 oligonucleotides each consisting of a different sequence of A and G nucleotides. This array was probed with a mixture comprising all 256 octapyrimidines, each end labelled by means of polynucleotide kinase and Y-$^{32}$P-ATP. Hybridisation was performed for 6-8 hours at 4° C.

In consecutive experiments the hybridisation solvent was changed through the series 1 M NaCl (containing 10 mM Tris.HCl pH 7.5, 1 mM EDTA, 7% sarcosine) and 2 M, 2.5 M, 3 M, 3.5 M, 4 M, 4.5 M, 5 M and 5.5 M TMACl (all containing 50 mM Tris.HCl pH 8.0, 2 mM EDTA, SDS at less than 0.04 mg/ml). The plate was rinsed for 10 minutes at 4° C. in the respective solvent to remove only loosely matched molecules, sealed in a plastic bag and exposed to a PhorphorImager storage phosphor screen at 4° C. overnight in the dark.

The following table quotes relative signal intensities, at a given salt concentration, of hybrids formed with oligonucleotides of varying a content. In this table, the first row refers to the oligonucleotide GGGGGGGG, and the last row to the oligonucleotide AAAAAAAA. It can be seen that the difference in response of these two oligonucleotides is marked in 1 M NaCl, but much less marked in 3M or 4M TMACl.

| Relative Intensities at given Salt Concentration | | | |
| --- | --- | --- | --- |
| | Number of A's | | |
| Solvent | 0 | 4 | 8 |
| 1M NaCl | 100 | 30 | 20 |
| 2M TMACl | 100 | 70 | 30 |
| 3M TMACl | 70 | 100 | 40 |
| 4M TMACl | 60 | 100 | 40 |

The following table indicates relative signal intensities obtained, with octamers containing 4A's and 4G's, at different hybridisation salt concentrations. It can been seen that the signal intensity is dramatically increased at higher concentrations of TMACl.

| Relative Intensities at different Salt Concentrations | |
| --- | --- |
| Solvent | Yield of hybrid |
| 1M NaCl | 100 |
| 2M TMACl | 200 |
| 3M TMACl | 700 |
| 4M TMACl | 2000 |

In conclusion, we have demonstrated the following:

1. It is possible to synthesise oligonucleotides in good yield on a flat glass plate.
2. Multiple sequences can be synthesised on the sample in small spots, at high density, by a simple manual procedure, or automatically using a computer controlled device.
3. Hybridisation to the oligonucleotides on the plate can be carried out by a very simple procedure. Hybridisation is efficient, and hybrids can be detected by a short autoradiographic exposure.
4. Hybridisation is specific. There is no detectable signal on areas of the plate where there are no oligonucleotides. We have tested the effects of mismatched bases, and found that a single mismatched base at any position in oligonucleotides ranging in length from 12-mer to 19-mer reduces the stability of the hybrid sufficiently that the signal can be reduced to a very low level, while retaining significant hybridisation to the perfectly matched hybrid.
5. The oligonucleotides are stably bound to the glass and plates can be used for hybridisation repeatedly.

The invention thus provides a novel way of analysing nucleotide sequences, which should find a wide range of application. We list a number of potential applications below:

Small Arrays of Oligonucleotides as Fingerprinting and Mapping Tools.

Analysis of Known Mutations Including Genetic Diseases.

Example 4 above shows how the invention may be used to analyse mutations. There are many applications for such a method, including the detection of inherited diseases.

Genetic Fingerprinting.

In the same way as mutations which lead to disease can be detected, the method could be used to detect point mutations in any stretch of DNA. Sequences are now available for a number of regions containing the base differences which lead to restriction fragment length polymorphism (RFLPs). An array of oligonucleotides representing such polymorphisms could be made from pairs of oligonucleotides representing the two allelic restriction sites. Amplification of the sequence containing the RFLP, followed by hybridisation to the plate, would show which alleles were present in the test genome. The number of oligonucleotides that could be analysed in a single analysis could be quite large. Fifty pairs made from selected alleles would be enough to give a fingerprint unique to an individual.

Linkage Analysis.

Applying the method described in the last paragraph to a pedigree would pinpoint recombinations. Each pair of spots in the array would give the information that is seen in the track of the RFLP analysis, using gel electrophoresis and blotting, that is now routinely used for linkage studies. It should be possible to analyse many alleles in a single analysis, by hybridisation to an array of allelic pairs of oligonucleotides, greatly simplifying the methods used to find linkage between a DNA polymorphism and phenotypic marker such as a disease gene.

The examples above could be carried out using the method we have developed and confirmed by experiments.

Large Arrays of Oligonucleotides as Sequence Reading Tools.

We have shown that oligonucleotides can be synthesised in small patches in precisely determined positions by one of two methods: by delivering the precursors through the pen of a pen-plotter, or by masking areas with silicone rubber. It is obvious how a pen plotter could be adapted to synthesise large arrays with a different sequence in each position. For some applications the array should be a predetermined, limited set; for other applications, the array should comprise every sequence of a predetermined length. The masking method can be used for the latter by laying down the precursors in a mask which produces intersecting lines. There are many ways in which this can be done and we give one example for illustration:

1. The first four bases, A, C, G, T, are laid in four broad stripes on a square plate.
2. The second set is laid down in four stripes equal in width to the first, and orthogonal to them. The array is now composed of all sixteen dinucleotides.
3. The third and fourth layers are laid down in four sets of four stripes one quarter the width of the first stripes. Each set of four narrow stripes runs within one of the broader stripes. The array is now composed of all 256 tetranucleotides.
4. The process is repeated, each time laying down two layers with stripes which are one quarter the width of the previous two layers. Each layer added increases the length of the oligonucleotides by one base, and the number of different oligonucleotide sequences by a factor of four.

The dimensions of such arrays are determined by the width of the stripes. The narrowest stripe we have laid is 1 mm, but this is clearly not the lowest limit.

There are useful applications for arrays in which part of the sequence is predetermined and part made up of all possible sequences. For example:

Characterising mRNA Populations.

Most mRNAs in higher eukaryotes have the sequence AAUAAA close to the 3' end. The array used to analyse mRNAs would have this sequence all over the plate. To analyse a mRNA population it would be hybridised to an array composed of all sequences of the type $N_m$AATAAAN$_n$. For m+n=8, which should be enough to give a unique oligonucleotide address to most of the several thousand mRNAs that is estimated to be present in a source such as a mammalian cell, the array would be 256 elements square. The 256×256 elements would be laid on the AATAAA using the masking method described above. With stripes of around 1 mm, the array would be ca. 256 mm square.

This analysis would measure the complexity of the mRNA population and could be used as a basis for comparing populations from different cell types. The advantage of this approach is that the differences in the hybridisation pattern would provide the sequence of oligonucleotides that could be used as probes to isolate all the mRNAs that differed in the populations.

Sequence Determination.

To extend the idea to determine unknown sequences, using an array composed of all possible oligonucleotides of a chosen length, requires larger arrays than we have synthesised to date. However, it is possible to scale down the size of spot and scale up the numbers to those required by extending the methods we have developed and tested on small arrays. Our experience shows that the method is much simpler in operation than the gel based methods.

TABLE 1

For Examples 3 and 4 array (a) was set out as follows:

| | | | |
|---|---|---|---|
| 20 GAG GAC TCC TCT ACG | | 20 GAG GAC aCC TCT ACG | |
| 36 GAG GAC TCC TCT GAC G | | 20 GAC GAC aCC TCT GAC G | |
| 36 GAG GAC TCC TCT AGA CG | | 20 GAC GAC aCC TCT AGA CG | |
| 47 GAG GAC TCC TCT CAG ACG | | 36 GAG GAC aCC TCT CAG ACG | |
| 60 GAG GAC TCC TCT TCA GAC G | | 47 GAG GAC aCC TCT TCA GAC G | |
| 56 .AG GAC TCC TCT TCA GAC G | | 42 .AG GAC aCC TCT TCA GAC G | |
| 56 ..G GAC TCC TCT TCA GAC G | | 42 ..G GAC aCC TCT TCA GAC G | |
| 47 ... GAC TCC TCT TCA GAC G | | 42 ... GAC aCC TCT TCA GAC G | |
| 42 ... .AC TCC TCT TCA GAC G | | 36 ... .AC aCC TCT TCA GAC G | |
| 36 ... ..C TCC TCT TCA GAC G | | 36 ... ..C aCC TCT TCA GAC G | |
| 36 ... ... TCC TCT TCA GAC G | | 36 ... ... aCC TCT TCA GAC G | |
| 36 ... ... .CC TCT TCA GAC G | | 36 ... ... .CC TCT TCA GAC G | |

For example 3 array (b) was set out as follows:

| | | |
|---|---|---|
| 20 GAG GAt TC | 20 GAG GAC TC | 20 GAG GAC aC |
| 20 GAG GAt TC | 20 GAG GAC TCC | 20 GAG GAC aCC |
| 20 GAG GAt TCC T | 20 GAG GAC TCC T | 20 GAG GAC aCC T |
| 20 GAG GAt TCC TC | 20 GAG GAC TCC TC | 20 GAG GAC aCC TC |
| 20 GAG GAt TCC TCT | 20 GAG GAC TCC TCT | 20 GAG GAC aCC TCT |
| 20 GAG GAt TCC TCT T | 20 GAG GAC TCC TCT T | 20 GAG GAC aCC TCT T |
| 20 GAG GAt TCC TCT TC | 20 GAG GAC TCC TCT TC | 20 GAG GAC aCC TCT TC |
| 20 GAG GAt TCC TCT TCA | 20 GAG GAC TCC TCT TCA | 20 GAG GAC aCC TCT TCA |
| 32 GAG GAt TCC TCT TCA G | 42 GAG GAC TCC TCT TCA G | 20 GAG GAC aCC TCT TCA G |
| 32 GAG GAt TCC TCT TCA GA | 47 GAG GAC TCC TCT TCA GA | 32 GAG GAC aCC TCT TCA GA |
| 42 GAG GAt TCC TCT TCA GAC | 52 GAG GAC TCC TCT TCA GAC | 42 GAG GAC aCC TCT TCA GAC |
| 52 GAG GAt TCC TCT TCA GAC G | 60 GAG GAC TCC TCT TCA GAC G | 52 GAG GAC aCC TCT TCA GAC G |
| 42 .AG GAt TCC TCT TCA GAC G | 52 .AG GAC TCC TCT TCA GAC G | 42 .AG GAC aCC TCT TCA GAC G |
| 42 ..G GAt TCC TCT TCA GAC G | 52 ..G GAC TCC TCT TCA GAC G | 42 ..G GAC aCC TCT TCA GAC G |
| 37 ... GAt TCC TCT TCA GAC G | 47 ... GAC TCC TCT TCA GAC G | 37 ... GAC aCC TCT TCA GAC G |
| 32 ... .At TCC TCT TCA GAC G | 42 ... .AC TCC TCT TCA GAC G | 32 ... .AC aCC TCT TCA GAC G |
| 32 ... ..t TCC TCT TCA GAC G | 42 ... ..C TCC TCT TCA GAC G | 32 ... ..C aCC TCT TCA GAC G |
| 32 ... ... TCC TCT TCA GAC G | 32 ... ... TCC TCT TCA GAC G | 32 ... ... aCC TCT TCA GAC G |

Between the three columns of array (b) listed above, were two columns, in which bases 6 and 7 from the left were missing in every line. These sequences all melted at 20 or 32 degrees. (a,t) mismatch base (.) missing base.

The invention claimed is:

1. Apparatus for analysing a polynucleotide, the apparatus comprising: a support having an impermeable surface; porous material attached to the impermeable surface; and an array of oligonucleotides with predetermined sequences attached to the porous material, wherein the array comprises at least two defined cells, the sequence of the oligonucleotides of a first cell is different from the sequence of the oligonucleotides of a second cell, the oligonucleotides are shorter than the polynucleotide, and the oligonucleotides are synthesized in situ.

2. Apparatus of claim 1, wherein the porous material is a microporous material.

3. Apparatus of claim 1, wherein the support is made of a silicon oxide.

4. Apparatus of claim 3, wherein the support is made of glass.

5. Apparatus of claim 1, comprising between 72 and $1.1 \times 10^{12}$ cells.

6. Apparatus of claim 1, wherein each cell holds at least $3 \times 10^{-12}$ µmol of oligonucleotide.

7. Apparatus of claim 1, wherein the oligonucleotides are covalently attached to the porous material.

8. Apparatus of claim 7, wherein the oligonucleotides are covalently attached by a terminal nucleotide.

9. Apparatus of claim 1, wherein the apparatus is manufactured using a computer-controlled device.

10. Apparatus of claim 9, wherein the computer-controlled device is a printing device.

11. A method of analyzing a polynucleotide, which method comprises:
   applying a labeled polynucleotide to be analyzed or a fragment thereof to the apparatus according to claim 1 under hybridization conditions, and
   analyzing the polynucleotide by observing the regions where the polynucleotide or fragment thereof hybridizes and the regions where the polynucleotide or fragment.

12. A method of comparing polynucleotide sequences, which method comprises: applying the polynucleotides to the apparatus according to claim 1 under hybridizing conditions, and observing the differences between the patterns of hybridization.

13. Apparatus for analysing a polynucleotide, the apparatus comprising: a support having an impermeable surface; porous material attached to the impermeable surface; and an array of oligonucleotides with predetermined sequences attached to the porous material, wherein the array comprises at least two defined cells, the sequence of the oligonucleotides of a first cell is different from the sequence of the oligonucleotides of a second cell, the oligonucleotides are shorter than the polynucleotide, wherein the oligonucleotides are covalently attached to the porous material by a terminal nucleotide.

14. Apparatus of claim 13, wherein the porous material is a microporous material.

15. Apparatus of claim 13, wherein the support is made of a silicon oxide.

16. Apparatus of claim 15, wherein the support is made of glass.

17. Apparatus of claim 13, comprising between 72 and $1.1 \times 10^{12}$ cells.

18. Apparatus of claim 13, wherein each cell holds at least $3 \times 10^{-12}$ µmol of oligonucleotide.

19. Apparatus of claim 13, wherein the apparatus is manufactured using a computer-controlled device.

20. Apparatus of claim 19, wherein the computer-controlled device is a printing device.

21. A method of analyzing a polynucleotide, which method comprises: applying a labeled polynucleotide to be analyzed or a fragment thereof to the apparatus according to claim 13 under hybridization conditions, and analysing the polynucleotide by observing the regions where the polynucleotide or fragment thereof hybridizes and the regions where the polynucleotide or fragment.

22. A method of comparing polynucleotide sequences, which method comprises: applying the polynucleotides to the apparatus according to claim 13 under hybridizing conditions, and observing the differences between the patterns of hybridization.

* * * * *

UNITED STATES PATENT AND TRADEMARK OFFICE
CERTIFICATE OF CORRECTION

PATENT NO. : 7,888,494 B2
APPLICATION NO. : 10/772467
DATED : February 15, 2011
INVENTOR(S) : Edwin Southern It is certified that error appears in the above-identified patent and that said Letters Patent is hereby corrected as shown below:

Title Pg, Item (73) Assignee, please change "Oxford Gene Therapy Limited, Oxford (GB)" to -- Oxford Gene Technology Limited, Oxford (GB) --.

Column 42, claim 11, line 3, please change "to be analyzed or a" to -- or --;

line 6, after "polynucleotide" insert -- or fragment thereof --;

line 8, after "fragment" insert -- thereof does not hybridize --.

Column 42, claim 12, line 61, please delete "the" (first occurrence).

Column 44, claim 21, line 6, please delete "to be analyzed";

line 7, delete "a";

line 9, change "analysing" to -- analyzing --; and after "polynucleotide" insert -- or fragment thereof--;

line 9, after "fragment" insert -- thereof does not hybridize --.

Column 44, claim 22, line 15, please delete "the" (first occurrence).

Signed and Sealed this
Fifth Day of April, 2011

David J. Kappos
*Director of the United States Patent and Trademark Office*

```
                               SEQUENCE LISTING

<160> NUMBER OF SEQ ID NOS: 76

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
aggtcgccgc cc                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
aggtctccgc cc                                                          12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3
gggcggcgac ct                                                          12

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
ctcctgagga gaagtctgc                                                   19

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
gaggactcct ctacg                                                       15

<210> SEQ ID NO 6
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      Oligonucleotide

<400> SEQUENCE: 6
gaggactcct ctgacg                                                     16

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7
gaggactcct ctagacg                                                    17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 8
gaggactcct ctcagacg                                                   18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
gaggactcct cttcagacg                                                  19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
aggactcctc ttcagacg                                                   18

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
ggactcctct tcagacg                                                    17

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
```

-continued

Oligonucleotide

<400> SEQUENCE: 12
gactcctctt cagacg                                                  16

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 13
actcctcttc agacg                                                   15

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14
ctcctcttca gacg                                                    14

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 15
tcctcttcag acg                                                     13

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 16
cctcttcaga cg                                                      12

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 17
gaggacacct ctacg                                                   15

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

```
<400> SEQUENCE: 18
gacgacacct ctgacg                                                    16

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19
gacgacacct ctagacg                                                   17

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
gaggacacct ctcagacg                                                  18

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
gaggacacct cttcagacg                                                 19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22
aggacacctc ttcagacg                                                  18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23
ggacacctct tcagacg                                                   17

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide
```

```
<400> SEQUENCE: 24
gacacctctt cagacg                                                    16

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 25
acacctcttc agacg                                                     15

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 26
cacctcttca gacg                                                      14

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 27
acctcttcag acg                                                       13

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 28
cctcttcaga cg                                                        12

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 29
gaggattcct                                                           10

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 30
```
gaggattcct c                                                    11

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 31
gaggattcct ct                                                   12

<210> SEQ ID NO 32
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 32
gaggattcct ctt                                                  13

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 33
gaggattcct cttc                                                 14

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 34
gaggattcct cttca                                                15

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 35
gaggattcct cttcag                                               16

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 36
gaggattcct cttcaga    17

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 37
gaggattcct cttcagac    18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 38
gaggattcct cttcagacg    19

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 39
aggattcctc ttcagacg    18

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 40
ggattcctct tcagacg    17

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 41
gattcctctt cagacg    16

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 42
attcctcttc agacg    15

-continued

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 43
ttcctcttca gacg                                                        14

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 44
tcctcttcag acg                                                         13

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 45
gaggactcct                                                             10

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 46
gaggactcct c                                                           11

<210> SEQ ID NO 47
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 47
gaggactcct ct                                                          12

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 48
gaggactcct ctt                                                         13

```
<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 49
gaggactcct cttc                                                       14

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 50
gaggactcct cttca                                                      15

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 51
gaggactcct cttcag                                                     16

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 52
gaggactcct cttcaga                                                    17

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 53
gaggactcct cttcagac                                                   18

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 54
gaggactcct cttcagacg                                                  19
```

```
<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 55
aggactcctc ttcagacg                                                 18

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 56
ggactcctct tcagacg                                                  17

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 57
gactcctctt cagacg                                                   16

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 58
actcctcttc agacg                                                    15

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 59
ctcctcttca gacg                                                     14

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 60
tcctcttcag acg                                                      13

<210> SEQ ID NO 61
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 61
gaggacacct                                                          10

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 62
gaggacacct c                                                        11

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 63
gaggacacct ct                                                       12

<210> SEQ ID NO 64
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 64
gaggacacct ctt                                                      13

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 65
gaggacacct cttc                                                     14

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 66
gaggacacct cttca                                                    15

<210> SEQ ID NO 67
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 67
gaggacacct cttcag                                              16

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 68
gaggacacct cttcaga                                             17

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 69
gaggacacct cttcagac                                            18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 70
gaggacacct cttcagacg                                           19

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 71
aggacacctc ttcagacg                                            18

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 72
ggacacctct tcagacg                                             17

<210> SEQ ID NO 73
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      Oligonucleotide

<400> SEQUENCE: 73
gacacctctt cagacg                                                         16

<210> SEQ ID NO 74
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 74
acacctcttc agacg                                                          15

<210> SEQ ID NO 75
<211> LENGTH: 14
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 75
cacctcttca gacg                                                           14

<210> SEQ ID NO 76
<211> LENGTH: 13
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 76
acctcttcag acg                                                            13
```